United States Patent [19]

Ford et al.

[11] 4,146,631
[45] Mar. 27, 1979

[54] BENZAMIDE DERIVATIVES

[75] Inventors: Roger E. Ford, Gidea Park; Philip Knowles, Rayleigh; Edward Lunt, Westcliff-on-Sea; Stuart M. Marshall, Stanford-le-Hope; Anthony J. H. Summers, London, all of England

[73] Assignee: May & Baker Limited, Essex, England

[21] Appl. No.: 848,032

[22] Filed: Nov. 3, 1977

[30] Foreign Application Priority Data

Nov. 5, 1976 [GB] United Kingdom ............... 46174/76

[51] Int. Cl.² .................... A61K 31/41; C07D 257/06
[52] U.S. Cl. .............................. 424/269; 260/308 D
[58] Field of Search .................... 260/308 D; 424/269

[56] References Cited
U.S. PATENT DOCUMENTS

| 2,750,393 | 6/1956 | Elpern | 260/308 D |
| 3,342,826 | 9/1967 | Miller et al. | 260/326.47 |
| 3,966,965 | 6/1976 | Sellstedt et al. | 424/269 |

Primary Examiner—Nicholas S. Rizzo
Assistant Examiner—D. B. Springer
Attorney, Agent, or Firm—Stevens, Davis, Miller & Mosher

[57] ABSTRACT

Benzamide derivatives of the formula:-

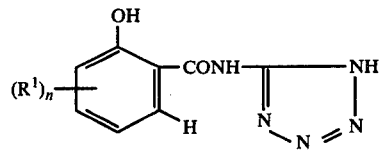

wherein $R^1$ represents a fluorine, chlorine or bromine atom, or an alkyl, alkoxy, alkylthio, alkylsulphonyl, alkanoylamino, alkylamino or alkylsulphamoyl group, each such group containing from 1 to 6 carbon atoms, a dialkylsulphamoyl, dialkylamino or dialkylcarbamoyl group (wherein the two alkyl groups may be the same or different and each contains from 1 to 4 carbon atoms), an alkanoyl, alkoxycarbonyl, alkoxycarbonylamino or alkylcarbamoyl group containing from 2 to 6 carbon atoms, or a hydroxy, formyl, nitro, trifluoromethyl, aryl, benzyloxycarbonylamino, amino, sulphamoyl, cyano, tetrazol-5-yl, carboxy, carbamoyl or aroyl group, and n represents an integer 1, 2 or 3, are new compounds possessing pharmacological properties, in particular properties of value in the treatment of respiratory disorders manifested by the interaction of tissue-fixed antibodies with specific antigens.

32 Claims, No Drawings

BENZAMIDE DERIVATIVES

This invention relates to new therapeutically useful benzamide derivatives, to processes for their preparation and to pharmaceutical compositions containing them.

As a result of research and experimentation, it has been found that the new benzamide derivatives represented by the general formula:

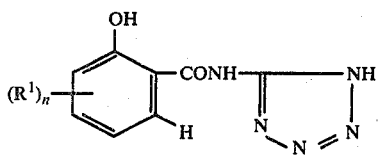

I

[wherein $R^1$ represents a fluorine, chlorine or bromine atom, or a straight- or branched-chain alkyl, alkoxy, alkylthio, alkylsulphonyl, alkanoylamino, alkylamino or alkylsulphamoyl group, each such group containing from 1 to 6 carbon atoms, a dialkylsulphamoyl, dialkylamino or dialkylcarbamoyl group (wherein the two alkyl groups may be the same or different and each contains from 1 to 4 carbon atoms), a straight- or branched-chain alkanoyl, alkoxycarbonyl, alkoxycarbonylamino or alkylcarbamoyl group containing from 2 to 6 carbon atoms, or a hydroxy, formyl, nitro, trifluoromethyl, aryl (e.g. phenyl), benzyloxycarbonylamino, amino, sulphamoyl, cyano, tetrazol-5-yl, carboxy, carbamoyl or aroyl (e.g. benzoyl) group, and n represents an integer 1, 2 or 3, preferably 1 or 2, the substituents $R^1$ being the same or different when n represents 2 or 3] and pharmaceutically acceptable salts thereof, possess valuable pharmacological properties.

It will be understood by those skilled in the art that each of the hydrogen atoms depicted in general formula I in the moieties OH, CONH and NH may give rise to tautomerism and that all the resulting tautomeric forms may be present to a greater or lesser degree and are in a state of dynamic equilibrium with each other. Furthermore, the substituents $R^1$ may contain chiral centres and thus give rise to optical isomerism. The present invention embraces all optical isomers of general formula I and all tautomers of compounds of general formula I and mixtures thereof.

The present invention includes pharmaceutically acceptable salts of compounds of formula I with pharmaceutically acceptable bases. By the term "pharmaceutically acceptable salts" is meant salts the cations of which are relatively innocuous to the animal organism when used in therapeutic doses so that the beneficial pharmacological properties of the parent compounds of general formula I are not vitiated by side effects ascribable to those cations. Suitable salts include the alkali metal, e.g. sodium and potassium, and ammonium salts and salts of amines known in the art to be pharmaceutically acceptable, e.g. ethylene diamine, choline, diethanolamine, triethanolamine, octadecylamine, diethylamine, triethylamine, 2-amino-2-(hydroxymethyl)propane-1,3-diol and 1-(3,4-dihydroxyphenyl)-2-isopropylaminoethanol.

Pharmaceutically acceptable salts may be prepared by the reaction together of a compound of formula I and the appropriate base, that is to say a base as described immediately hereinbefore, for example at an elevated temperature, with or without an appropriate solvent, preferably followed by recrystailization from an appropriate solvent, for example a hydroxylic solvent, e.g. water, of the salt so formed.

In this specification when reference is made to compounds of formula I reference is also intended to their pharmaceutically acceptable salts, where the context so permits.

The benzene derivatives of the present invention possess valuable pharmacological properties, in particular properties of value in the treatment of respiratory disorders manifested by the interaction of tissue-fixed antibodies with specific antigens, such as allergic bronchial asthma.

Individual compounds of formula I of particular importance include the following:

| | |
|---|---|
| 2-hydroxy-4-nitro-N-(tetrazol-5-yl)benzamide; | AA |
| 2-hydroxy-5-(N,N-dimethylsulphamoyl)-N-(tetrazol-5-yl)benzamide; | AB |
| 2-hydroxy-5-(N-methyl-N-isopropylsulphamoyl)-N-(tetrazol-5-yl)benzamide; | AC |
| 5-chloro-2-hydroxy-N-(tetrazol-5-yl)benzamide; | AL |
| 2-hydroxy-3,5-dinitro-N-(tetrazol-5-yl)benzamide; | AE |
| 2,5-dihydroxy-N-(tetrazol-5-yl)benzamide; | AF |
| 2-hydroxy-5-methyl-N-(tetrazol-5-yl)benzamide; | AG |
| 2-hydroxy-3-methyl-N-(tetrazol-5-yl)benzamide; | AH |
| 2-hydroxy-3-nitro-N-(tetrazol-5-yl)benzamide; | AI |
| 2,4-dihydroxy-N-(tetrazol-5-yl)benzamide; | AJ |
| 2-hydroxy-4-methyl-N-(tetrazol-5-yl)benzamide; | AK |
| 3-bromo-2-hydroxy-N-(tetrazol-5-yl)benzamide; | AL |
| 3-chloro-2-hydroxy-N-(tetrazol-5-yl)benzamide; | AM |
| 2-hydroxy-3-propoxy-N-(tetrazol-5-yl)benzamide; | AN |
| 2-hydroxy-5-nitro-N-(tetrazol-5-yl)benzamide; | AO |
| 2-hydroxy-5-methoxy-N-(tetrazol-5-yl)benzamide; | AP |
| 5-(N,N-dibutylsulphamoyl)-2-hydroxy-N-(tetrazol-5-yl)benzamide; | AQ |
| 3-acetyl-2-hydroxy-5-methyl-N-(tetrazol-5-yl)benzamide; | AR |
| 3-ethoxy-2-hydroxy-N-(tetrazol-5-yl)benzamide; | AS |
| 2-hydroxy-4-methoxy-N-(tetrazol-5-yl)benzamide; | AT |
| 3-acetyl-5-chloro-2-hydroxy-N-(tetrazol-5-yl)benzamide; | AU |
| 5-acetyl-2-hydroxy-N-(tetrazol-5-yl)benzamide; | AV |
| 3,5-diacetyl-2,4-dihydroxy-N-(tetrazol-5-yl)benzamide; | AW |
| 4-chloro-2-hydroxy-N-(tetrazol-5-yl)benzamide; | AX |
| 3,5-dibromo-2-hydroxy-N-(tetrazol-5-yl)benzamide; | AY |
| 5-acetylamino-2-hydroxy-N-(tetrazol-5-yl)benzamide; | AZ |
| 4-tert-butyl-2-hydroxy-N-(tetrazol-5-yl)benzamide; | BA |
| 4-acetylamino-2-hydroxy-N-(tetrazol-5-yl)benzamide; | BB |
| 4-trifluoromethyl-2-hydroxy-N-(tetrazol-5-yl)benzamide; | BC |
| 4-fluoro-2-hydroxy-N-(tetrazol-5-yl)benzamide; | BD |
| 2-hydroxy-3-methoxy-N-(tetrazol-5-yl)benzamide; | BE |
| 2-hydroxy-5-methylthio-N-(tetrazol-5-yl)benzamide; | BF |
| 2-hydroxy-5-phenyl-N-(tetrazol-5-yl)benzamide; | BG |
| 5-fluoro-2-hydroxy-N-(tetrazol-5-yl)benzamide; | BH |
| 2-hydroxy-3-methylthio-N-(tetrazol-5-yl)benzamide; | BI |
| 2-hydroxy-3-methylsulphonyl-N-(tetrazol-5-yl)benzamide; | BJ |
| 2-hydroxy-3,5-bis(methylsulphonyl)-N-(tetrazol-5-yl)benzamide | BK |
| 5-formyl-2-hydroxy-N-tetrazol-5-yl)benzamide; | BL |
| 5-bromo-2-hydroxy-N-(tetrazol-5-yl)benzamide; | BM |
| 2-hydroxy-4-methylthio-N-(tetrazol-5-yl)benzamide; | BN |
| 2-hydroxy-5-methylsulphonyl-N-(tetrazol-5-yl)benzamide; | BO |
| 2-hydroxy-4-methylsulphonyl-N-(tetrazol-5-yl)benzamide; | BP |
| 5-benzyloxycarbonylamino-2-hydroxy-N-(tetrazol-5-yl)benzamide; | BQ |
| 4-benzyloxycarbonylamino-2-hydroxy-N-(tetrazol5-yl)benzamide; | BR |
| 5-amino-2-hydroxy-N-(tetrazol-5-yl)benzamide; | BS |
| 3-(N-tert-butylsulphamoyl)-2-hydroxy-5-methyl-N-(tetrazol-5-yl)benzamide; | BT |
| 3-acetyl-2-hydroxy-5-sulphamoyl-N-(tetrazol-5-yl)benzamide; | BU |
| 5-trifluoromethyl-2-hydroxy-N-(tetrazol-5-yl)benzamide; | BV |
| 3-acetyl-5-ethyl-2-hydroxy-N-(tetrazol-5-yl)benzamide; | BW |
| 3-acetyl-2-hydroxy-4,5-dimethyl-N-(tetrazol-5-yl)benzamide; | BX |
| 3-acetyl-5-sec-butyl-2-hydroxy-N-(tetrazol-5-yl)benzamide; | BY |
| 3-acetyl-5-tert-butyl-2-hydroxy-N-(tetrazol-5-yl)benzamide; | BZ |
| 3-acetyl-2-hydroxy-N-(tetrazol-5-yl)benzamide; | CA |
| 3-acetyl-5-bromo-2-hydroxy-N-(tetrazol-5-yl)benzamide; | CB |
| 3-acetyl-5-fluoro-2-hydroxy-N-(tetrazol-5-yl)- | |

-continued

| | |
|---|---|
| benzamide; | CC |
| 3-acetyl-2-hydroxy-5-propyl-N-(tetrazol-5-yl)benzamide; | CD |
| 2-hydroxy-5-methyl-3-proprionyl-N-(tetrazol-5-yl)-benzamide; | CE |
| 5-ethyl-2-hydroxy-3-proprionyl-N-(tetrazol-5-yl)-benzamide; | CF |
| 3-butyl-5-ethyl-2-hydroxy-N-(tetrazol-5-yl)benzamide; | CG |
| 3-formyl-2-hydroxy-N-(tetrazol-5-yl)benzamide; | CH |
| 3-formyl-2-hydroxy-5-methyl-N-(tetrazol-5-yl)benzamide; | CI |
| 3-cyano-2-hydroxy-N-(tetrazol-5-yl)benzamide; | CJ |
| 5-cyano-2-hydroxy-N-(tetrazol-5-yl)benzamide; | CK |
| 3-cyano-2-hydroxy-5-methyl-N-(tetrazol-5-yl)benzamide; | CL |
| 2-hydroxy-5-methyl-3,N-bis(tetrazol-5-yl)benzamide; | CM |
| 3-N-(tetrazol-5-yl)carbamoylsalicylic acid; | CN |
| 3-tert-butylcarbamoyl-2-hydroxy-N-(tetrazol-5-yl)-benzamide; | CO |
| 2-hydroxy-3-dimethylamino-N-(tetrazol-5-yl)benzamide; | CP |
| 5-acetyl-2-hydroxy-3-nitro-N-(tetrazol-5-yl)benzamide; | CQ |
| 3-benzoyl-2-hydroxy-5-methyl-N-(tetrazol-5-yl)-benzamide and | CR |
| 3acetyl-2-hydroxy-5-nitro-N-(tetrazol-5-yl)benzamide, and their pharmaceutically acceptable salts. | CS |

The letters of the alphabet AA to CS are assigned to the compounds for easy reference later in the specification, for example in the following Tables.

Preferred compounds of general formula I are those wherein $R^1$ represents a fluorine, chlorine or bromine atom, or a straight- or branched-chain alkyl, alkoxy, alkylthio, alkylsulphonyl, alkanoylamino or alkylsulphamoyl group, each such group containing from 1 to 6 carbon atoms, a dialkylsulphamoyl or dialkylamino group (wherein the two alkyl groups may be the same or different and each contains from 1 to 4 carbon atoms), a straight- or branched-chain alkanoyl or alkylcarbamoyl group containing from 2 to 6 carbon atoms, or a hydroxy, formyl, nitro, trifluoromethyl, phenyl, benzyloxycarbonylamino, amino, sulphamoyl, cyano, tetrazol-5-yl, carboxy or benzoyl group, and n is as hereinbefore defined, and more particularly those such compounds wherein n represents 1 or 2, and their pharmaceutically acceptable salts.

Compounds within general formula I wherein one of the substituents $R^1$ on the phenyl ring is a nitro, cyano, alkanoyl (e.g. acetyl, propionyl or butyryl), formyl or tetrazol-5-yl group, any other substituent(s) $R^1$ present (preferably not more than one) being as hereinbefore defined, and their pharmaceutically acceptable salts, are of particular importance. Within that class compounds AE, AI, AO, BL, BU, BY, BZ, CC, CG, CH, CJ, CK, CQ, and especially compounds AR, BW, CA, CD, CE, CF, CM and CS, are of outstanding importance. Compounds AN, AP, BB, BF, BR and, especially, BE outside that class are also of outstanding importance.

In pharmacological tests the benzamide derivatives of general formula I suppress the passive cutaneous anaphylactic (PCA) reaction resulting from combination of tissue-fixed reaginic antibodies with the appropriate antigenic material (termed reagin-allergen combination) and carried out in an essentially similar manner to that described by Ogilvie [Nature (Lond.), (1964), 204, 91–92; Immunology, (1967), 12, 112–131]. In the method used to test these compounds sera were obtained from rats which had been infected with larvae of the nematode parasite Nippostrongylus brasiliensis; as a result of the parasitic infestation reaginic antibodies are elaborated in the host mammal and are found in sera removed from such animals. Other, non-infected, rats received intradermal injections of appropriate dilutions of such sera and were then given the allergenic material along with Evans' blue dye intravenously forty-eight hours later.

The allergenic material consisted of supernatant fluid after centrifugation of homogenates of adult Nippostrongylus brasiliensis worms which had been macerated in Tyrode's solution. The sites of PCA reactions were visualised by the effusion of Evan's blue dye from the circulation into those areas as a result of increased capillary permeability caused by the release of biologically-active substances from cells where reagin-allergen combination had occurred. The new compounds when given intravenously to the rats just before injection of allergen, or administered orally thirty minutes before intravenous injection of allergen, were able to prevent the development of the PCA reaction, as shown below in Table I, Table II and Table III.

Table I shows the intravenous dose, expressed in mg/kg animal body weight, which produces 100% inhibition of the PCA reaction (ED100).

Table II shows the percentage inhibition of the PCA reaction produced by an oral dose of 100 mg/kg animal body weight.

Table III shows the oral dose, expressed in mg/kg animal body weight, which produces 50% inhibition of the PCA reaction (ED50).

TABLE I

| Compound | AA | AB | AC | AD | AE | AF | AG | AH | AI |
|---|---|---|---|---|---|---|---|---|---|
| ED100 | 10 | 2 | 5 | 1 | 0.05 | 1 | 1 | 0.5 | 0.5 |
| Compound | AJ | AK | AL | AM | AN | AO | AP | AR | AS |
| ED100 | 10 | 10 | 10 | 5 | 0.5 | 0.2 | 0.5 | 0.1 | 1 |
| Compound | AT | AU | AV | AW | AY | AZ | BA | BB | BD |
| ED100 | 5 | 2 | 10 | 5 | 5 | 10 | 10 | 1 | 10 |
| Compound | BE | BF | BG | BH | BI | BJ | BK | BL | BM |
| ED100 | 0.2 | 0.5 | 10 | 1 | 20 | 20 | 10 | 0.5 | 5 |
| Compound | BN | BO | BQ | BR | BS | BU | BV | BW | BX |
| ED100 | 10 | 5 | 5 | 0.5 | 5 | 0.5 | 2 | 0.1 | 20 |
| Compound | BY | BZ | CA | CB | CC | CD | CE | CF | CG |
| ED100 | 0.5 | 0.5 | 0.1 | 2 | 0.2 | 0.1 | 0.05 | 0.05 | 0.1 |
| Compound | CH | CI | CJ | CK | CL | CM | CN | CO | CP |
| ED100 | 0.5 | 2 | 0.5 | 0.2 | 2 | 0.05 | 1 | 5 | 2 |
| Compound | CQ | CR | CS | | | | | | |
| ED100 | 0.2 | 1 | 0.1 | | | | | | |

TABLE II

| Compound | AA | AC | AD | AE | AH | AI | AJ | AK |
|---|---|---|---|---|---|---|---|---|
| % inhibition | 18 | 20 | 94 | 80 | 82 | 68 | 38 | 32 |
| Compound | AL | AM | AN | AO | AP | AR | AS | AT |
| % inhibition | 69 | 82 | 87 | 48 | 75 | 42 | 76 | 8 |
| Compound | AU | AV | AW | AY | BA | BB | BD | BE |
| % inhibition | 71 | 16 | 84 | 65 | 37 | 26 | 75 | 62 |
| Compound | BH | BJ | BK | BL | BM | BN | BO | BS |
| % inhibition | 94 | 64 | 29 | 25 | 46 | 8 | 63 | 35 |
| Compound | BU | BV | BW | BY | BZ | CA | CB | CC |
| % inhibition | 86 | 90 | 51 | 43 | 59 | 64 | 66 | 62 |
| Compound | CD | CE | CF | CG | CH | CI | CJ | CK |
| % inhibition | 64 | 99 | 41 | 55 | 75 | 70 | 50 | 89 |
| Compound | CL | CM | CN | CO | CP | CQ | CR | CS |
| % inhibition | 26 | 64 | 43 | 26 | 68 | 56 | 22 | 54 |

TABLE III

| Compound | AD | AE | AH | AI | AL | AM | AN | AO |
|---|---|---|---|---|---|---|---|---|

TABLE III-continued

| pound ED50 | 13 | 0.1-0.45 | 10 | 5-30 | 55 | 85 | 40 | 100 |
|---|---|---|---|---|---|---|---|---|
| Compound | AP | AR | AS | AU | BE | BH | BM | BV | BW |
| ED50 | 100 | 0.75 | 10 | 1.8 | 18 | 16 | 65 | 37 | 0.1 |
| Compound | BY | BZ | CB | CC | CE | CF | CG | CH | CI |
| ED50 | 1.8 | 2.6 | 64 | 1.9 | 0.4 | 0.27 | 2.2 | 5.3 | 5.4 |
| Compound | CJ | CK | CN | CP | | | | | |
| ED50 | 37 | 50 | 20 | 26 | | | | | |

The utility of the benzamide derivatives of general formula I is enhanced by the fact that they are only of very low toxicity to mammals, demonstrated by the results obtained in the following tests:

Acute oral toxicity in mice

Mice were each treated orally with one of the compounds of formula I, and they were observed daily until there had been at least 3 consecutive days without any deaths. The LD50 figures obtained (doses lethal to 50% of mice tested) are shown below in Table IV, expressed in mg/kg animal body weight.

TABLE IV

| Compound | AD | AE | AG | AH | AI | AL |
|---|---|---|---|---|---|---|
| LD50 | >1000 | >1000 | >1000 | >1000 | >1000 | 794 |
| Compound | AN | AO | AP | AQ | AR | AS |
| LD50 | >1000 | >1000 | >1000 | >1000 | >1000 | >1000 |
| Compound | AU | AV | AW | AX | BA | BB |
| LD50 | >1000 | >1000 | >1000 | >1000 | >1000 | >1000 |
| Compound | BE | BG | BH | BT | BW | BX |
| LD50 | >1000 | >1000 | >1000 | >1000 | >1000 | >1000 |
| Compound | BY | BZ | CA | CD | CE | CF |
| LD50 | >1000 | >1000 | >1000 | >1000 | >1000 | >1000 |
| Compound | CG | CJ | CQ | CR | CS | |
| LD50 | >1000 | >1000 | >1000 | >1000 | >1000 | |

The symbol ">" means "greater than" in this specification. Where the LD50 is said to be ">1000," a more precise estimation of the LD50 was not possible because the numbers of deaths was too small, even at the highest dose used, 1000 mg/kg.

Acute intravenous toxicity in mice

Mice were each treated intravenously with an aqueous solution of the triethanolamine salt or sodium salt of one of the compounds of formula I, and they were observed until there had been at least 3 consecutive days without any deaths. The LD50 figures obtained (doses lethal to 50% of mice tested) are shown below in Table V, expressed in mg/kg animal body weight. In Table V, "Na" means that the sodium salt was used and "T" means that the triethanolamine salt was used.

The aqueous solutions were prepared as follows:

Triethanolamine salts

A mixture of the test compound and water was treated gradually with triethanolamine until complete solution occurred. The solution was then diluted with water to a concentration of test compound of either 1% w/v or 2% w/v.

Sodium salts

The test compound was dissolved in aqueous sodium hydroxide (1N) and the solution was brought to pH 8 by treatment with hydrochloric acid. The solution was then diluted with water to a concentration of test compound of 2% w/v.

Various volumes of these solutions were then administered to the mice.

TABLE V

| Compound | AD | AE | AG | AH | AI | AL | AN | AO | AP | AQ | AR | AS | AU |
|---|---|---|---|---|---|---|---|---|---|---|---|---|---|
| salt | Na | T | Na | T | T | T | T | T | Na | Na | T | T | T |
| concentration of test solution (%w/v) | 2 | 2 | 2 | 2 | 2 | 2 | 2 | 2 | 2 | 2 | 2 | 2 | 2 |
| LD50 | 480 | 490 | 670 | 770 | >1000 | 540 | 480 | 870 | 950 | 280 | 430 | 560 | 245 |
| Compound | AV | AW | AX | BA | BB | BE | BG | BH | BI | BT | BW | BX | BY |
| salt | T | T | T | T | T | T | T | T* | T | Na | Na | T | T |
| concentration of test solution (%w/v) | 2 | 2 | 2 | 2 | 2 | 2 | 1 | 1 or 2 | 2 | 2 | 2 | 2 | 2 |
| LD50 | 645 | 710 | 260 | 230 | 645 | 580 | 200 | 500 | 580 | 500 | 320 | 870 | 180 |
| Compound | BZ | CA | CD | CE | CF | CG | CJ | CQ | CR | CS | | | |
| salt | T | T | T | T | T | T* | T | T | T | T | | | |
| concentration of test solution (%w/v) | 2 | 2 | 2 | 2 | 2 | 1 or 2 | 2 | 2 | 2 | 2 | | | |
| LD50 | 240 | 500 | 250 | 270 | 280 | 270 | >1000 | 890 | 350 | 780 | | | |

*for lower doses 1% w/v solution was used, and for higher doses 2% w/v was used.

The benzamide derivatives of general formula I may be prepared by the application or adaptation of known methods. By the term "known methods," as used in this specification, is meant methods heretofore used or described in the literature.

Thus, according to a feature of the present invention, compounds of formula I (except those wherein $R^1$ represents an alkylamino or amino groups) are prepared by the reaction of 5-aminotetrazole with carboxylic acids of the general formula:

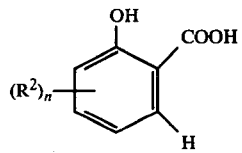

[wherein $R^2$ represents a fluorine, chlorine or bromine atom, or a straight- or branched-chain alkyl, alkoxy, alkylthio, alkylsulphonyl, alkanoylamino or alkylsulphamoyl group, each such group containing from 1 to 6 carbon atoms, a dialkylsulphamoyl, dialkylamino or dialkylcarbamoyl group (wherein the two alkyl groups may be the same or different and each contains from 1 to 4 carbon atoms), a straight- or branched-chain alkanoyl, alkoxycarbonyl, alkoxycarbonylamino or alkylcarbamoyl group containing from 2 to 6 carbon atoms, or a hydroxy, formyl, nitro, trifluoromethyl, aryl (e.g. phenyl), benzyloxycarbonylamino, sulphamoyl, cyano, tetrazol-5-yl, carboxy, carbamoyl or aroyl (e.g. benzoyl) group, and n represents an integer 1, 2 or 3, preferably 1 or 2, the substituents $R^2$ being the same or different when n represents 2 or 3],
or (except those wherein $R^1$ in formula I represents an alkylamino, hydroxy, amino or carboxy group) with esters thereof of the general formula:

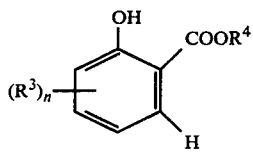

[wherein $R^3$ represents a fluorine, chlorine or bromine atom, or a straight- or branched-chain alkyl, alkoxy, alkylthio, alkylsulphonyl, alkanoylamino or alkylsulphamoyl group, each such group containing from 1 to 6 carbon atoms, a dialkylsulphamoyl, dialkylamino or dialkylcarbamoyl group (wherein the two alkyl groups may be the same or different and each contains from 1 to 4 carbon atoms), a straight- or branched-chain alkanoyl, alkoxycarbonyl, alkoxycarbonylamino or alkylcarbamoyl group containing from 2 to 6 carbon atoms, or a formyl, nitro, trifluoromethyl, aryl (e.g. phenyl), benzyloxycarbonylamino, sulphamoyl, cyano, tetrazol-5-yl, carbamoyl or aroyl (e.g. benzoyl) group, and n represents an integer 1, 2 or 3, preferably 1 or 2, the substituents $R^3$ being the same or different when n represents 2 or 3 and $R^4$ represents a straight- or branched-chain alkyl group containing from 1 to 4 carbon atoms],
or (except those wherein $R^1$ in formula I represents an alkanoylamino, alkylamino, alkoxycarbonylamino, hydroxy, benzyloxycarbonylamino, amino, carboxy or carbamoyl group) with acid halides thereof of the general formula:

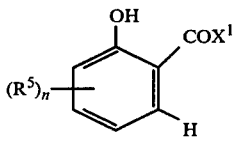

[wherein $R^5$ represents a fluorine, chlorine or bromine atom, or a straight- or branched-chain alkyl, alkoxy, alkylthio, alkylsulphonyl or alkylsulphamoyl group, each such group containing from 1 to 6 carbon atoms, a dialkylsulphamoyl, dialkylamino or dialkylcarbamoyl group (wherein the two alkyl groups may be the same or different and each contains from 1 to 4 carbon atoms), a straight- or branched-chain alkanoyl, alkoxycarbonyl or alkylcarbamoyl group containing from 2 to 6 carbon atoms, or a formyl, nitro, trifluoromethyl, aryl (e.g. phenyl), sulphamoyl, cyano, tetrazol-5-yl or aroyl (e.g. benzoyl) group, and n represents an integer 1, 2 or 3, preferably 1 or 2, the substituents $R^5$ being the same or different when n represents 2 or 3, and $X^1$ represents a chlorine or bromine atom].

The reaction between 5-aminotetrazole and carboxylic acids of formula II may be carried out in the presence of a condensation agent such as N,N'-dicyclohexylcarbodiimide or (except when $R^2$ represents an alkanoylamino, alkoxycarbonylamino, hydroxy, benzyloxycarbonylamino, carboxy or carbamoyl group) phosphorus trichloride, preferably in the presence of an inert solvent such as pyridine, benzene, toluene or xylene, preferably in dry conditions, at temperatures between, for example, 10° C. and 100° C.

The reaction between 5-aminotetrazole and esters of formula III may be carried out with or without a solvent, for example a lower alkanol (e.g. methanol), an aromatic solvent (e.g. xylene) or dimethylformamide, preferably at elevated temperatures, and optionally in the presence of an alkali metal alkoxide containing from 1 to 4 carbon atoms.

Esters of formula III may be prepared from the corresponding carboxylic acids of formula II by the application or adaptation of known methods for the esterification of 2-carboxyphenols such as salicylic acid.

The reaction between acid halides of formula IV (which may be prepared from the corresponding carboxylic acids within formula II by the application or adaptation of known methods, for example by reaction with thionyl chloride, phosphorus trichloride or oxalyl chloride, optionally in situ) and 5-aminotetrazole is preferably carried out in an inert organic solvent, for example benzene, toluene, xylene or pyridine, and preferably at elevated temperatures, for example the reflux temperature of the reaction mixture.

As a further feature of the invention, compounds of formula I (except those wherein $R^1$ represents an alkylthio, formyl, nitro or benzyloxycarbonylamino groups) are prepared by reduction of compounds of the general formula:

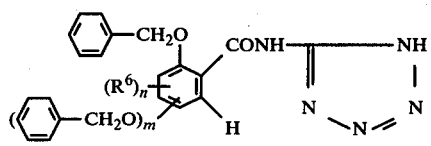

wherein $R^6$ represents a fluorine, chlorine or bromine atom, or a straight- or branched-chain alkyl, alkoxy, alkylsulphonyl, alkanoylamino, alkylamino or alkylsulphamoyl group, each such group containing from 1 to 6 carbon atoms, a dialkylsulphamoyl, dialkylamino or dialkylcarbamoyl group (wherein the two alkyl groups may be the same or different and each contains from 1 to 4 carbon atoms), a straight- or branched-chain alkanoyl, alkoxycarbonyl, alkoxycarbonylamino or alkylcarbamoyl group containing from 2 to 6 carbon atoms, or a hydroxy, trifluoromethyl, aryl (e.g. phenyl), amino, sulphamoyl, cyano, tetrazol-5-yl, carboxy, carbamoyl or aroyl (e.g. benzoyl) group, and q represents zero or an integer 1, 2 or 3, preferably 1 or 2, the substituents $R^6$ being the same or different when q represents 2 or 3, and m represents zero or 1 and the sum of m and q is 1, 2 or 3. Generally reduction is carried out by hydrogenation in the presence of a catalyst such as palladium on charcoal in an organic solvent, for example N-methylpyrrolid-2-one or ethanol.

According to a further feature of the invention, compounds of formula I (except those wherein $R^1$ represents an alkanoylamino, alkylamino, alkoxycarbonylamino, hydroxy, benzyloxycarbonylamino, amino, carboxy or carbamoyl group) are prepared by the reaction of compounds of the general formula:

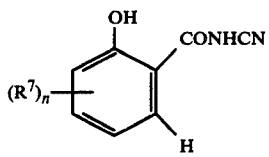

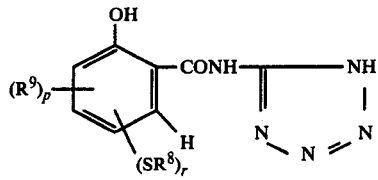

[wherein R[7] represents a fluorine, chlorine or bromine atom, or a straight- or branched-chain alkyl, alkoxy, alkylthio, alkylsulphonyl or alkylsulphamoyl group, each such group containing from 1 to 6 carbon atoms, a dialkylsulphamoyl, dialkylamino or dialkylcarbamoyl group (wherein the two alkyl groups may be the same or different and each contains from 1 to 4 carbon atoms), a straight- or branched-chain alkanoyl, alkoxycarbonyl or alkylcarbamoyl group containing from 2 to 6 carbon atoms, or a formyl, nitro, trifluoromethyl, aryl (e.g. phenyl), sulphamoyl, cyano, tetrazol-5-yl or aroyl (e.g. benzoyl) group, and n represents an integer 1, 2 or 3, preferably 1 or 2, the substituents R[7] being the same or different when n represents 2 or 3] with hydrazoic acid or a salt thereof, for example sodium azide, potassium azide or ammonium azide.

Generally the reaction is carried out in an organic solvent, e.g. N-methylpyrrolid-2-one, preferably at a temperature between 0° C. and 120° C.

Compounds of formula VI may be prepared by reaction of compounds of formula IV with cyanamide. Preferably the reaction is carried out in an inert solvent in the presence of an acid-binding agent, for example pyridine, which may also serve as reaction medium.

As a further feature of the invention, compounds of the general formula:

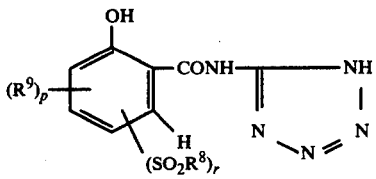

[wherein R[8] represents a straight- or branched-chain alkyl group containing from 1 to 6 carbon atoms, r represents an integer 1, 2 or 3, R[9] represents a fluorine, chlorine or bromine atom, or a straight- or branched-chain alkyl, alkoxy, alkylsulphonyl, alkanoylamino or alkylsulphamoyl group, each such group containing from 1 to 6 carbon atoms, a dialkylsulphamoyl or dialkylcarbamoyl group (wherein the two alkyl groups may be the same or different and each contains from 1 to 4 carbon atoms), a straight- or branched-chain alkanoyl, alkoxycarbonyl, alkoxycarbonylamino or alkylcarbamoyl group containing from 2 to 6 carbon atoms, or a nitro, trifluoromethyl, aryl (e.g. phenyl), benzyloxycarbonylamino, sulphamoyl, cyano, tetrazol-5-yl, carboxy, carbamoyl or aroyl (e.g. benzoyl) group, and p represents zero or the integer 1 or 2, the substituents R[9] being the same or different when p represents 2, or R[9] represents a hydroxy group in the para-position relative to the tetrazolylcarbamoyl group, and the sum of r and p is 1, 2 or 3] within general formula I are prepared by the oxidation of compounds of the general formula:

(wherein R[8], R[9], r and p are as hereinbefore defined) to convert the alkylthio group(s) of formula —SR[8] to alkylsulphonyl. The oxidation may be carried out by the action of a peroxy acid, for example m-chloroperbenzoic acid, in an inert solvent, e.g. sulpholane, or alternatively by the action of aqueous hydrogen peroxide solution, preferably in the presence of a carboxylic acid (e.g. acetic acid) and optionally at elevated temperature.

As a further feature of the invention, compounds of the general formula:

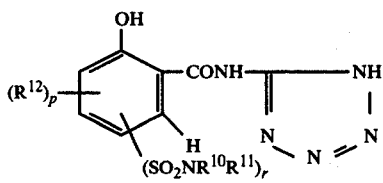

[wherein R[10] and R[11] are the same or different and each represents a hydrogen atom or a straight- or branched-chain alkyl group containing from 1 to 4 carbon atoms, r represents an integer 1, 2 or 3, R[12] represents a fluorine, chlorine or bromine atom, or a straight- or branched-chain alkyl, alkoxy, alkylthio or alkylsulphonyl group, each such group containing from 1 to 6 carbon atoms, or a dialkylamino group (wherein the two alkyl groups may be the same or different and each contains from 1 to 4 carbon atoms), a straight- or branched-chain alkanoyl or alkoxycarbonyl group containing from 2 to 6 carbon atoms, or a hydroxy, formyl, nitro, trifluoromethyl, aryl (e.g. phenyl), cyano, tetrazol-5-yl, carboxy or aroyl (e.g. benzoyl) group, and p represents zero or the integer 1 or 2, the substituents R[12] being the same or different when p represents 2, and the sum of r and p is 1, 2 or 3] within general formula I are prepared by reacting an amine of the general formula:

HNR[10]R[11]    X (wherein R[10] and R[11] are as hereinbefore defined) with a compound of the general formula:

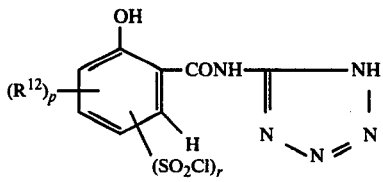

wherein R[12], r and p are as hereinbefore defined. The reaction may be carried out in an organic solvent, e.g. ethanol, at ambient or elevated temperature.

Compounds of formula XI may be prepared by the action of chlorosulphonic acid on compounds of the general formula:

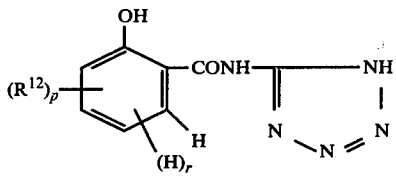

XII wherein $R^{12}$, r and p are as hereinbefore defined.

As will be apparent to those skilled in the art, the position or positions of the group or groups —($SO_2R^{10}R^{11})_r$ which may be introduced in this manner can depend upon the nature and position of the substituent(s) —$R^{12})_p$ — if present — and upon the reaction conditions employed in converting compounds of formula XII to compounds of formula XI, and may be determined by a minimum amount of experimentation.

As a further feature of the present invention, compounds of the general formula:

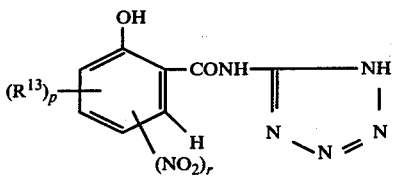

XIII

[wherein $R^{13}$ represents a fluorine, chlorine or bromine atom or a straight- or branched-chain alkyl, alkoxy, alkylsulphonyl, alkanoylamino, alkylamino or alkylsulphamoyl group containing from 1 to 6 carbon atoms, a dialkylsulphamoyl, dialkylamino, or dialkylcarbamoyl group (wherein the two alkyl groups may be the same or different and each contains from 1 to 4 carbon atoms), a straight- or branched-chain alkanoyl, alkoxycarbonyl, alkoxycarbonylamino or alkylcarbamoyl group containing from 2 to 6 carbon atoms, or a hydroxy, formyl, nitro, trifluoromethyl, amino, sulphamoyl, cyano, tetrazol-5-yl, carboxy or carbamoyl group, and p represents zero or the integer 1 or 2, the substituents $R^{13}$ being the same or different when p represents 2, r represents 1, 2 or 3, and the sum of r and p is 1, 2 or 3] within general formula I are prepared by the nitration of compounds of the general formula:

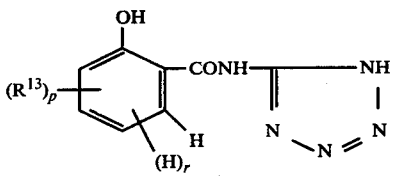

XIV (wherein $R^{13}$, r and p are as hereinbefore defined) by the application or adaptation of known methods for the nitration of phenyl moieties, for example by the action of a mixture of concentrated nitric acid and concentrated sulphuric acid.

As will be apparent to those skilled in the art, the position or positions of the nitro group or groups which may be introduced in this manner depends upon the nature and position of the substituent(s) —$(R^{13})_p$ — if present — and upon the reaction conditions employed in the nitration, and may be determined with a minimum amount of experimentation.

According to a further feature of the present invention, compounds of the general formula:

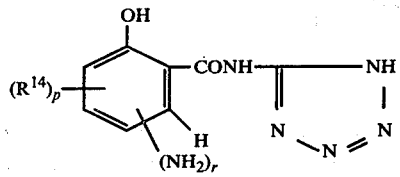

XV

[wherein $R^{14}$ represents a fluorine, chlorine or bromine atom, or a straight- or branched-chain alkyl, alkoxy, alkylthio, alkylsulphonyl, alkanoylamino, alkylamino or alkylsulphamoyl group, each such group containing from 1 to 6 carbon atoms, a dialkylsulphamoyl, dialkylamino or dialkylcarbamoyl group (wherein the two alkyl groups may be the same or different and each contains from 1 to 4 carbon atoms), a straight- or branched-chain alkanoyl or alkylcarbamoyl group containing from 2 to 6 carbon atoms, or a hydroxy, formyl, nitro, trifluoromethyl, aryl (e.g. phenyl), sulphamoyl, cyano, tetrazol-5-yl, carboxy, carbamoyl or aroyl (e.g. benzoyl) group, p represents zero or the integer 1 or 2, the substituents $R^{14}$ being the same or different when p represents 2, r represents 1, 2 or 3, and the sum of r and p is 1, 2 or 3] within general formula I are prepared by the reaction of compounds of the general formula:

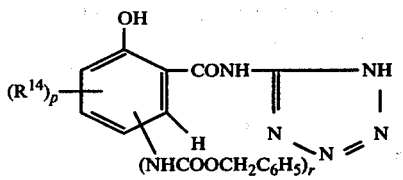

XVI (wherein $R^{14}$, r and p are as hereinbefore defined) within general formula I with acetic acid and hydrogen bromide.

The following Examples illustrate the preparation of the new compounds of the present invention.

The Reference Examples following thereafter illustrate the preparation of starting materials used in the Examples.

EXAMPLE 1

Compounds BE, AM, AU, BI, BJ, BK, BB, AZ, AX, BC, BD, BH BN, BF, BA, AA, BG, BM, AV, AY and BL A stirred mixture of 3-methoxysalicylic acid (16.8 g), anhydrous 5-aminotetrazole (16.8 g) and N,N'-dicyclohexylcarbodiimide (24.7 g) in dry pyridine (400 ml) was heated at 90° C. for 2 hours. A solid (i) was filtered off, and the pyridine was removed from the filtrate under reduced pressure, leaving a fawn solid (ii). Solids (i) and (ii) were combined, added to aqueous ammonia solution (2N) and stirred for 30 minutes. The mixture was filtered, the filtrate was treated with decolourizing charcoal and filtered again, and was then acidified to pH 1 by treatment with concentrated hydrochloric acid. The resulting solid was filtered off and recrystalized from a mixture of dimethylformamide and acetic acid to give 2-hydroxy-3-methoxy-N-(tetrazol-5-yl)benzamide (14.7 g), m.p. 265°–267° C. (with decomposition).

By proceeding in a similar manner, but replacing the 3-methoxysalicylic acid used as a starting material by the appropriate quantities of
3-chlorosalicylic acid,
3-acetyl-5-chlorosalicylic acid,
3-(methylthio)salicylic acid,
3-(methylsulphonyl)salicylic acid, and
3,5-bis(methylsulphonyl)salicylic acid,
respectively, and recrystallizing from the solvents which are indicated after their melting points, instead of from a mixture of dimethylformamide and acetic acid, there were prepared the following compounds:
3-chloro-2-hydroxy-N-(tetrazol-5-yl)benzamide, m.p. 249°–252° C. (with decomposition) (from ethanol);
3-acetyl-5-chloro-2-hydroxy-N-(tetrazol-5-yl)benzamide, m.p. 268°–270° C. (with decomposition) (from acetic acid);
2-hydroxy-3-methylthio-N-(tetrazol-5-yl)benzamide, m.p. 256°–257° C. (with decomposition) (from a mixture of dimethylformamide and acetic acid);
2-hydroxy-3-methylsulphonyl-N-(tetrazol-5-yl)benzamide, m.p. 245°–248° C. (with decomposition) (from a mixture of dimethylformamide and water), and
2-hydroxy-3,5-bis(methylsulphonyl)-N-(tetrazol-5-yl)benzamide, m.p. 252°–253° C. (with decomposition) (from a mixture of ethanol and water).

By again proceeding in a similar manner, but stirring the reactants together at 25° C. for 20 to 24 hours instead of at 90° C. for 2 hours, and replacing the 3-methoxysalicylic acid used as starting material by the appropriate quantities of
4-acetamidosalicylic acid,
5-acetamidosalicylic acid,
4-chlorosalicylic acid,
4-trifluoromethylsalicylic acid,
4-fluorosalicylic acid,
5-fluorosalicylic acid,
4-(methylthio)salicylic acid,
5-(methylthio)salicylic acid,
4-tert-butyl-salicylic acid,
4-nitrosalicylic acid,
5-phenylsalicylic acid,
5-bromosalicylic acid,
5-acetylsalicylic acid,
3,5-dibromosalicylic acid, and
5-formylsalicylic acid, respectively,
there were prepared:
4-acetamido-2-hydroxy-N-(tetrazol-5-yl)benzamide, m.p. 310°–312° C. (with decomposition) (from a mixture of N-methylpyrrolid-2-one and water);
5-acetamido-2-hydroxy-N-(tetrazol-5-yl)benzamide, m.p. 291°–293° C. (with decomposition) (from a mixture of dimethylformamide and water);
4-chloro-2-hydroxy-N-(tetrazol-5-yl)benzamide, m.p. 259°–260.5° C. (with decomposition) (from dimethylformamide);
4-trifluoromethyl-2-hydroxy-N-(tetrazol-5-yl)benzamide, m.p. 263°–265° C. (from acetic acid);
4-fluoro-2-hydroxy-N-(tetrazol-5-yl)benzamide, m.p. 248°–250° C. (from acetic acid);
5-fluoro-2-hydroxy-N-(tetrazol-5-yl)benzamide, m.p. 274° C. (with decomposition) (from a mixture of dimethylformamide and acetic acid);
2-hydroxy-4-methylthio-N-(tetrazol-5-yl)benzamide, m.p. 282°–284° C. (with decomposition) (from a mixture of dimethylformamide and water);
2-hydroxy-5-methylthio-N-(tetrazol-5-yl)benzamide, m.p. 261°–262° C. (with decomposition) (from a mixture of dimethylformamide and acetic acid);
4-tert-butyl-2-hydroxy-N-(tetrazol-5-yl)benzamide, m.p. 272°–274° C. (with decomposition) (not recrystallized but instead boiled in ethanol);
2-hydroxy-4-nitro-N-(tetrazol-5-yl)benzamide, m.p. 242°–245° C. (from a mixture of dimethylformamide and acetic acid);
2-hydroxy-5-phenyl-N-(tetrazol-5-yl)benzamide, m.p. 277°–278° C. (with decomposition) (from a mixture of dimethylformamide and acetic acid);
5-bromo-2-hydroxy-N-(tetrazol-5-yl)benzamide, m.p. 272°–274° C. (with decomposition) (from acetic acid);
5-acetyl-2-hydroxy-N-(tetrazol-5-yl)benzamide, m.p. 267°–269° C. (with decomposition) (from dimethylformamide and water);
3,5-dibromo-2-hydroxy-N-(tetrazol-5-yl)benzamide, m.p. 252°–253° C. (with decomposition) (from acetic acid), and
5-formyl-2-hydroxy-N-(tetrazol-5-yl)benzamide, m.p. 268° C. (with decomposition)
(this compound was recrystallized from a mixture of dimethylformamide and acetic acid, then dissolved in aqueous sodium carbonate solution. The solution was treated with hydrochloric acid and the resulting solid was filtered off and triturated with concentrated hydrochloric acid).

EXAMPLE 2

Compounds AD, AJ, AF, AG and AT

A solution of 2-benzyloxy-5-chloro-N-(tetrazol-5-yl)benzamide (2.7 g) in N-methylpyrrolid-2-one (50 ml) was hydrogenated at 25° C. and 5 kg/cm$^2$ pressure using a 5% w/w palladium on charcoal catalyst. The reaction mixture was filtered and then evaporated under vacuum and the resulting solid was triturated with water and then dried. This solid was boiled with ethanol (50 ml) for 10 minutes and the undissolved material was filtered off and washed with ethanol and with diethyl ether to give 5-chloro-2-hydroxy-N-(tetrazol-5-yl)benzamide (1.5 g), m.p. 266°–269° C. (with decomposition).

By proceeding in a similar manner, but replacing the 2-benzyloxy-5-chloro-N-(tetrazol-5-yl)benzamide used as starting material by the appropriate quantities of
2,4-dibenzyloxy-N-(tetrazol-5-yl)benzamide,
2,5-dibenzyloxy-N-(tetrazol-5-yl)benzamide,
2-benzyloxy-5-methyl-N-(tetrazol-5-yl)benzamide, and
2-benzyloxy-4-methoxy-N-(tetrazol-5-yl)benzamide,
respectively, and replacing the purification procedure described above by the procedures indicated below, there were prepared:
2,4-dihydroxy-N-(tetrazol-5-yl)benzamide, m.p. 281°–283° C. (with decomposition) (dissolved in aqueous sodium bicarbonate solution and precipitated therefrom by treatment with hydrochloric acid);
2,5-dihydroxy-N-(tetrazol-5-yl)benzamide, m.p. 299°–300° C. (with decomposition) (this compound was recrystallised from a mixture of dimethylformamide and water and then dissolved in saturated aqueous sodium bicarbonate solution. This solution was treated with hydrochloric acid and the resulting solid was filtered off);
2-hydroxy-5-methyl-N-(tetrazol-5-yl)benzamide, m.p. 289°–291° C. (with decomposition) (recrystallized from a mixture of dimethylformamide and water), and 2-hydroxy-4-methoxy-N-(tetrazol-5-yl)benzamide, m.p. 280°–281° C. (with decomposition) (recrystallised from a mixture of dimethylformamide and water).

EXAMPLE 3

Compounds AI, AH, AK, AG, AP, AL, AM, BE, AS and AN

Anhydrous 5-aminotetrazole (15 g) and phosphorus trichloride (6 ml) were added to a suspension of 3-nitrosalicylic acid (16 g) in dry benzene (250 ml). The mixture was stirred and heated at reflux for 20 hours. The mixture was then cooled and diluted with petroleum ether (b.p. 60°–80° C.; 250 ml) and the resulting solid was filtered off. The solid was treated with dilute hydrochloric acid (200 ml; 2N) and the mixture was stirred for 30 minutes, and the solid was then filtered off and washed with ethanol and dissolved in aqueous ammonia solution (2N). This solution was treated with decolourizing charcoal and filtered and the filtrate was acidified by treatment with concentrated hydrochloric acid to give 2-hydroxy-3-nitro-N-(tetrazol-5-yl)benzamide (5.0 g), m.p. 236°–238° C. (with decomposition).

By proceeding in a similar manner, but replacing the 3-nitrosalicylic acid used as a starting material by the appropriate quantities of
3-methylsalicylic acid,
4-methylsalicylic acid,
5-methylsalicylic acid,
5-methoxysalicylic acid,
3-bromosalicylic acid,
3-chlorosalicylic acid,
3-methoxysalicylic acid,
3-ethoxysalicylic acid, and
3-propoxysalicylic acid, respectively,
and replacing the purification procedure described above by the procedures described below, there were prepared:
2-hydroxy-3-methyl-N-(tetrazol-5-yl)benzamide, m.p. 264°–265° C. (recrystallized from a mixture of dimethylformamide and water);
2-hydroxy-4-methyl-N-(tetrazol-5-yl)benzamide, m.p. 288°–289° C. (with decomposition) (recrystallized from a mixture of dimethylformamide and water);
2-hydroxy-5-methyl-N-(tetrazol-5-yl)benzamide, m.p. 287°–289° C. (with decomposition) (recrystallized from a mixture of dimethylformamide and water);
2-hydroxy-5-methoxy-N-(tetrazol-5-yl)benzamide, m.p. 272°–274° C. (with decomposition) (recrystallized from a mixture of dimethylformamide and water);
3-bromo-2-hydroxy-N-(tetrazol-5-yl)benzamide, m.p. 248°–250° C. (recrystallized from a mixture of dimethylformamide and water);
3-chloro-2-hydroxy-N-(tetrazol-5-yl)benzamide, m.p. 250°–251° C. (with decomposition) (recrystallized from ethanol);
2-hydroxy-3-methoxy-N-(tetrazol-5-yl)benzamide, m.p. 265°–267° C. (with decomposition) (recrystallized from acetic acid);
3-ethoxy-2-hydroxy-N-(tetrazol-5-yl)benzamide, m.p. 257°–258° C. (with decomposition) (recrystallized from acetic acid), and
2-hydroxy-3-propoxy-N-(tetrazol-5-yl)benzamide, m.p. 230°–232° C. (with decomposition) (dissolved in 2N aqueous ammonia solution and precipitated therefrom by treatment with hydrochloric acid).

EXAMPLE 4

Compounds AO, AR and AW

Purified thionyl chloride (6 ml) was added to a suspension of dried 5-nitrosalicylic acid (3.6 g) in dry toluene (40 ml) and the mixture was stirred and heated at reflux for 90 minutes. The resulting clear orange-brown solution was evaporated in vacuo at below 40° C.

The residual oil was treated with dry toluene and again evaporated in vacuo and this procedure was repeated several times to remove the remaining thionyl chloride.

The 5-nitrosalicyloyl chloride thus obtained was dissolved in dry toluene (40 ml) and treated with anhydrous 5-aminotetrazole (3.4 g) and the mixture was stirred and heated at reflux for 12 hours. The mixture was then allowed to cool and was treated with petroleum ether (b.p. 40°–60° C.; 40 ml). The resulting solid was filtered off, washed with petroleum ether (b.p. 40°–60° C.) and stirred with hydrochloric acid (2N; 100 ml). The undissolved solid was filtered off, washed with hydrochloric acid (2N) and with water, and was then dried and dissolved in glacial acetic acid (750 ml). The solution was filtered hot and was then concentrated to 150 ml volume and was then cooled and filtered to give 2-hydroxy-5-nitro-N-(tetrazol-5-yl)-benzamide (2.2 g), m.p. 271°–272° C. (with decomposition).

By proceeding in a similar manner, but replacing the 5-nitrosalicylic acid used as a starting material by the appropriate quantities of
3-acetyl-5-methylsalicylic acid, and
3,5-diacetyl-2,4-dihydroxybenzoic acid, there were prepared:
3-acetyl-2-hydroxy-5-methyl-N-(tetrazol-5-yl)benzamide, m.p. 280°–282° C. (with decomposition) (recrystallized from a mixture of dimethylformamide and acetic acid); and
3,5-diacetyl-2,4-dihydroxy-N-(tetrazol-5-yl)benzamide, m.p. above 270° C. (with decomposition) (recrystallized from a mixture of dimethylformamide and acetic acid).

EXAMPLE 5

Compounds AB, AC and AQ

2-Hydroxy-N-(tetrazol-5-yl)benzamide (2.05 g) was added to chlorosulphonic acid (15 ml) during 15 minutes and the mixture was allowed to stand at 25° C. for 19 hours. The dark solution was then dropped cautiously on to a mixture of ice and water (100 ml), keeping the temperature below 3° C. The white precipitated solid was filtered off and washed well with water. The damp solid was added to a solution of dimethylamine in ethanol (33% w/v; 60 ml), and the solution was filtered and allowed to stand at 25° C. overnight. The mixture was then diluted with water (100 ml), acidified by treatment with concentrated hydrochloric acid, and cooled in ice. The resulting white solid was filtered off, washed with water, and recrystallized from ethanol to give 2-hydroxy-5-(N,N-dimethylsulphamoyl)-N-(tetrazol-5-yl)benzamide (2.0 g), m.p. 276°–278° C. (with decomposition).

By proceeding in a similar manner, but replacing the dimethylamine used as a starting material by the appropriate quantities of N-methylisopropylamine and dibutylamine, respectively, there were prepared 2-hydroxy-5-(N-methyl-N-isopropylsulphamoyl)-N-(tetrazol-5- yl)benzamide, m.p. 263°–265° C. (with decomposition) (recrystallized from ethanol), and 5-(N,N-dibutylsulphamoyl)-2-hydroxy-N-(tetrazol-5-yl)-benzamide, m.p. 240°–242° C. (recrystallized from a mixture of dimethylformamide and water).

EXAMPLE 6

Compound AE

2-Hydroxy-N-(tetrazol-5-yl)benzamide (5.12 g) was dissolved in concentrated sulphuric acid (50 ml) and the mixture was treated with concentrated nitric acid (d 1.42; 6.7 ml) and kept at 0° C. for 3 days. The dark solution was poured on to a mixture of ice and water (600 ml) and the resulting solid was centrifuged off, washed well with water, and dried to give 2-hydroxy-3,5-dinitro-N-(tetrazol-5-yl)benzamide (5.0 g), m.p. 234°–236° C. (with decomposition).

EXAMPLE 7

Compounds BP and BO

2-Hydroxy-4-methylthio-N-(tetrazol-5-yl)benzamide (0.5 g; prepared as described in Example 1) was stirred with acetic acid (5 ml) and hydrogen peroxide (2.5 ml; 30% w/w) was added. The mixture was heated at 100° C. for 20 hours and was then cooled. The solid was filtered off, washed with water and recrystallized from a mixture of dimethylformamide and water to give 2-hydroxy-4-methylsulphonyl-N-(tetrazol-5-yl)benzamide (0.4 g), m.p. 260°–273° C. (with decomposition).

By proceeding in a similar manner, but replacing the 2-hydroxy-4-methylthio-N-(tetrazol-5-yl)benzamide used as a starting material by the appropriate quantity of 2-hydroxy-5-methylthio-N-(tetrazol-5-yl)benzamide (prepared as described in Example 1), there was prepared 2-hydroxy-5-methylsulphonyl-N-(tetrazol-5-yl)benzamide m.p. 291°–292° C. (with decomposition) (recrystallized from acetic acid).

EXAMPLE 8

Compounds BQ and BR

By proceeding in a manner similar to that hereinbefore described in Example 1, but replacing the 3-methoxysalicylic acid used as starting material by the appropriate quantities of
5-benzyloxycarbonylaminosalicylic acid, and
4-benzyloxycarbonylaminosalicylic acid, respectively, stirring the reactants together at 25° C. for 20 to 24 hours, there were prepared:
5-benzyloxycarbonylamino-2-hydroxy-N-(tetrazol-5-yl)benzamide, m.p. 281°–282° C. (with decomposition) (from ethanol), and
4-benzyloxycarbonylamino-2-hydroxy-N-(tetrazol-5-yl)benzamide, m.p. above 360° C. (from acetic acid).

EXAMPLE 9

Compound BS

Acetic acid (100 ml) was saturated with hydrogen bromide at 10° C. and the mixture was treated with 5-benzyloxycarbonylamino-2-hydroxy-N-(tetrazol-5-yl)benzamide (1.77 g). The mixture was stirred at 25° C. for 20 hours, and then most of the hydrogen bromide was removed by passing a stream of air through the mixture for 6 hours. Any finely divided suspended solid was then removed by centrifuging and the supernatant liquid was decanted off. Removal of the acetic acid in vacuo gave a solid, which was triturated with diethyl ether and dried to give 5-amino-2-hydroxy-N-(tetrazol-5-yl)benzamide hydrobromide (1.0 g), m.p. above 330° C.

EXAMPLE 10

Compounds BT and BU

By proceeding in a manner similar to that hereinbefore described in Example 5, but replacing the 2-hydroxy-N-(tetrazol-5-yl)benzamide and dimethylamine, used as starting materials, by the appropriate quantities of
2-hydroxy-5-methyl-N-(tetrazol-5-yl)benzamide and tert-butylamine, and of
3-acetyl-2-hydroxy-N-(tetrazol-5-yl)benzamide and ammonia, respectively, there were prepared:
3-(N-tert-butylsulphamoyl)-2-hydroxy-5-methyl-N-(tetrazol-5-yl)benzamide, m.p. 249°–251° C. (with decomposition) (recrystallized from aqueous dimethylformamide), and
3-acetyl-2-hydroxy-5-sulphamoyl-N-(tetrazol-5-yl)benzamide, m.p. above 310° C. (darkening at 270° C.) (recrystallized from aqueous dimethylformamide).

EXAMPLE 11

Compound BV

2-Benzyloxy-5-trifluoromethyl-N-(tetrazol-5-yl)benzamide (2.7 g) was dissolved in ethanol (500 ml), and the solution was hydrogenated at 25° C. and 5 kg/cm$^2$ pressure, using a 5% palladium on charcoal catalyst. The reaction mixture was then filtered, and evaporated under vacuum. The resulting solid was recrystallized from isopropanol, with the aid of charcoal, to give 5-trifluoromethyl-2-hydroxy-N-(tetrazol-5-yl)benzamide (0.85 g), m.p. 245°–246° C. (with decomposition).

EXAMPLE 12

Compounds, BW, BX, BY, BZ, CA, CB, CC, CD, CE, CF, CG, CH, CI, CJ, CK, CL, CM, CN, CO, CP, CQ and CR A mixture of 3-acetyl-5-ethylsalicylic acid (55.0 g) and N,N'-dicyclohexylcarbodiimide (60.1 g) in dry pyridine (550 ml) was stirred at 25° C. for one hour. Anhydrous 5-aminotetrazole (24.7 g) was then added to the mixture, and stirring was continued at 60° C. for 24 hours. The pyridine was removed in vacuo, and the residue was treated with aqeuous ammonia solution (2N; 500 ml). The resulting slurry was stirred at between 90° and 100° C. for 15 minutes. The insoluble N,N'-dicyclohexylurea was filtered off, and the filtrate was acidified by treatment with concentrated hydrochloric acid. The resulting green precipitate was filtered off and recrystallized twice from aqueous dimethylformamide to give 3-acetyl-5-ethyl-2-hydroxy-N-(tetrazol-5-yl)benzamide (35.4 g), in the form of a pale yellow solid, m.p. 257°–258° C.

By proceeding in a similar manner but replacing the 3-acetyl-5-ethylsalicylic acid, used as a starting material, by the appropriate quantities of
3-acetyl-4,5-dimethylsalicylic acid;
3-acetyl-5-sec-butylsalicylic acid;
3-acetyl-5-tert-butylsalicylic acid;
3-acetylsalicylic acid;
3-acetyl-5-bromosalicylic acid;
3-acetyl-5-fluorosalicylic acid;
3-acetyl-5-propylsalicylic acid;
5-methyl-3-propionylsalicylic acid;
5-ethyl-3-propionylsalicylic acid;

3-butyryl-5-ethylsalicylic acid;
3-formylsalicylic acid;
3-formyl-5-methylsalicylic acid;
3-cyanosalicylic acid;
5-cyanosalicylic acid;
3-cyano-5-methylsalicylic acid;
5-methyl-3-(tetrazol-5-yl)salicylic acid;
2-hydroxyisophthalic acid;
3-tert-butylcarbamoylsalicylic acid;
3-dimethylaminosalicylic acid;
5-acetyl-3-nitrosalicylic acid, and
3-benzoyl-5-methylsalicylic acid, respectively, there were prepared:

3-acetyl-2-hydroxy-4,5-dimethyl-N-(tetrazol-5-yl)benzamide, m.p. 245°–247° C. (with decomposition);
3-acetyl-5-sec-butyl-2-hydroxy-N-(tetrazol-5-yl)benzamide, m.p. 228°–230° C. (with decomposition) (recrystallized from 90% w/w formic acid);
3-acetyl-5-tert-butyl-2-hydroxy-N-(tetrazol-5-yl)benzamide, m.p. 258°–260° C. (with decomposition) (recrystallized from 90% w/w formic acid);
3-acetyl-2-hydroxy-N-(tetrazol-5-yl)benzamide, m.p. 291°–292° C. (with decomposition);
3-acetyl-5-bromo-2-hydroxy-N-(tetrazol-5-yl)benzamide, m.p. 253°–254° C. (with decomposition);
3-acetyl-5-fluoro-2-hydroxy-N-(tetrazol-5-yl)benzamide, m.p. 268°–270° C. (with decomposition) (recrystallized from a mixture of dimethylformamide and acetic acid);
3-acetyl-2-hydroxy-5-propyl-N-(tetrazol-5-yl)benzamide, m.p. 257°–258° C. (with decomposition);
2-hydroxy-5-methyl-3-propionyl-N-(tetrazol-5-yl)benzamide, m.p. 280°–281° C. (with decomposition);
5-ethyl-2-hydroxy-3-propionyl-N-(tetrazol-5-yl)benzamide, m.p. 257°–258.5° C. (with decomposition);
3-butyryl-5-ethyl-2-hydroxy-N-(tetrazol-5-yl)benzamide, m.p. 253°–254° C. (with decomposition);
3-formyl-2-hydroxy-N-(tetrazol-5-yl)benzamide, m.p. 251°–254° C. (with decomposition) (recrystallized from formic acid);
3-formyl-2-hydroxy-5-methyl-N-(tetrazol-5-yl)benzamide, m.p. 238°–242° C. (with decomposition) (recrystallized from formic acid);
3-cyano-2-hydroxy-N-(tetrazol-5-yl)benzamide, m.p. 259°–260° C. (with decomposition);
5-cyano-2-hydroxy-N-(tetrazol-5-yl)benzamide, m.p. 310°–312° C. (with decomposition) (recrystallized from acetic acid);
3-cyano-2-hydroxy-5-methyl-N-(tetrazol-5-yl)benzamide, m.p. 243°–245° C. (with decomposition) (recrystallized from a mixture of dimethylformamide and acetic acid);
2-hydroxy-5-methyl-3,N-bis-(tetrazol-5-yl)benzamide hydrate, m.p. above 360° C.;
3-N-(tetrazol-5-yl)carbamoylsalicylic acid, m.p. 257°–259° C. (with decomposition);
3-tert-butylcarbamoyl-2-hydroxy-N-(tetrazol-5-yl)benzamide, m.p. 285°–287° C. (with decomposition) (recrystallized from a mixture of dimethylformamide and acetic acid);
2-hydroxy-3-dimethylamino-N-(tetrazol-5-yl)benzamide, m.p. 262°–263° C. (with decomposition) (recrystallized from acetic acid);
5-acetyl-2-hydroxy-3-nitro-N-(tetrazol-5-yl)benzamide, m.p. 248°–249° C. (with decomposition) (recrystallized from aqueous dimethylsulphoxide), and
3-benzoyl-2-hydroxy-5-methyl-N-(tetrazol-5-yl)benzamide, m.p. 274°–275° C. (with decomposition).

EXAMPLE 13

Compound CS

3-Acetyl-2-hydroxy-N-(tetrazol-5-yl)benzamide (6.0 g) was dissolved in concentrated sulphuric acid (30 ml). The solution was then cooled to 0° C. and, with stirring, was treated with concentrated nitric acid (density 1.42; 1.62 ml) at such a rate that the temperature did not exceed 10° C. The mixture was left to stand at between 0° and 5° C. for 20 hours, and was then poured into a mixture of ice and water (300 ml). The precipitated solid was collected, washed with water, and recrystallized from 98% w/w formic acid to give 3-acetyl-2-hydroxy-5-nitro-N-tetrazol-5-yl)benzamide, m.p. 255° C. (with decomposition).

REFERENCE EXAMPLE 1

By the application or adaptation of the methods described by Baine et al, J. Org. Chem., 1954, 19, 510 to the appropriate starting materials, there were prepared:
3-(methylthio)salicyclic acid, m.p. 168°–170° C.;
4-tert-butyl-salicylic acid, m.p. 138°–141° C.;
3-methylsalicylic acid, m.p. 169°–170° C.;
4-methylsalicylic acid, m.p. 176°–178° C.;
5-methylsalicylic acid, m.p. 150°–152° C.;
3-bromosalicylic acid, m.p. 183°–184° C., and
3-chlorosalicylic acid, m.p. 171°–174° C., respectively.

REFERENCE EXAMPLE 2

A mixture of 3-(methylthio)salicylic acid (2.0 g), glacial acetic acid (18 ml) and hydrogen peroxide (6 ml; 30 w/w) was heated at 95°–100° C. for 18 hours. The solvents were then removed in vacuo and the residue was recrystallized from water, with the aid of charcoal, to give 3-methylsulphonylsalicylic acid (1.5 g), m.p. 179.5°–180.5° C.

REFERENCE EXAMPLE 3

(a) An intimate mixture of 3,5-bis(chlorosulphonyl)salicylic acid (54.1 g) and sodium bicarbonate (75.5 g) was added portionwise during 30 minutes to a stirred solution of anhydrous sodium sulphite (81 g) and sodium bicarbonate (5.4 g) in water (500 ml) at 60°–70° C. and the mixture was stirred for a further 30 minutes. Methanol (550 ml) was then added, followed by methyl iodide (108 ml). The mixture was stirred and heated at reflux for 24 hours. An excess of aqueous sodium hydroxide solution (50% w/w) was added and the methanol was distilled off during one hour. The mixture was then acidified with aqueous sulphuric acid (50% w/v), with cooling, to give a crystalline solid, which was filtered off and recrystallized from water to give 3,5-bis(methylsulphonyl)salicylic acid (24.4 g), m.p. 267°–271° C. (with decomposition).

(b) The 3,5-bis(chlorosulphonyl)salicylic acid used as a starting material was obtained as follows:

Salicylic acid (10 g) was added to chlorosulphonic acid (60 ml) during 5 minutes. The mixture was then heated at 130°–140° C. for 90 minutes. After cooling, the mixture was cooled and then added dropwise to an excess of a mixture of ice and water, keeping the temperature below 0° C. The precipitated solid was extracted with dichloromethane, and the organic extract was dried over sodium sulphate, and concentrated in vacuo to a small volume and treated with petroleum ether (b.p. 40°–60° C.). The precipitate was filtered off and recrystallized from a large volume of toluene to give 3,5-bis(chlorosulphonyl)salicylic acid (9.95 g), m.p. 185°–187° C.

REFERENCE EXAMPLE 4

The preparation of 5-bromosalicylic acid was carried out by the application of the method described for its preparation by Hewitt et al, J. Chem. Soc., 1904, 85, 1228.

The insoluble solid remaining from the crystallization from water in that preparation was recrystallized from aqueous ethanol to give 3,5-dibromosalicylic acid, m.p. 220° C.

REFERENCE EXAMPLE 5

(a) Dry 2-benzyloxy-5-chlorobenzoic acid (1.15 g) was treated, with stirring, with dry pyridine (20 ml) and anhydrous 5-aminotetrazole (3.72 g). The mixture was stirred at 25° C. and treated dropwise with silicon tetrachloride (0.45 g), and the mixture was then stirred at 25° C. for 20 hours. The resulting clear yellow solution was cautiously poured into a mixture of ice and water (50 ml) and the mixture was acidified to pH 1 by treatment with concentrated hydrochloric acid. The white precipitated solid was filtered off, washed with water, with ethanol and with diethyl ether, and recrystallized from a mixture of dimethylformamide and water to give 2-benzyloxy-5-chloro-N-(tetrazol-5-yl)benzamide, (0.29 g), m.p. 256°–257° C. (with decomposition).

By proceeding in a similar manner, but replacing the 2-benzyloxy-5-chlorobenzoic acid used as a starting material by the appropriate quantities of 2,4-dibenzyloxybenzoic acid;
2,5-dibenzyloxybenzoic acid;
2-benzyloxy-5-methylbenzoic acid, and
2-benzyloxy-4-methoxybenzoic acid, respectively, there were prepared:

2,4-dibenzyloxy-N-(tetrazol-5-yl)benzamide, m.p. 247°–250° C. (with decomposition) (recrystallized from dimethylformamide);

2,5-dibenzyloxy-N-(tetrazol-5-yl)benzamide, m.p. 252°–253° C. (with decomposition) (recrystallized from aqueous dimethylformamide);

2-benzyloxy-5-methyl-N-(tetrazol-5-yl)benzamide, m.p. 258.5°–259.5° C. (with decomposition) (recrystallized from aqueous dimethylformamide), and 2-benzyloxy-4-methoxy-N-(tetrazol-5-yl)benzamide, m.p. 254°–256° C. (with decomposition) (recrystallized from dimethylformamide).

(b)(i) The 2-benzyloxy-5-chlorobenzoic acid used as a starting material was prepared as follows:

A mixture of 5-chlorosalicyclic acid (7.7 g), benzyl chloride (10.35 ml), anhydrous potassium carbonate (6.2 g), and dry sulpholane (100 ml) was stirred and heated in an oil bath at 120° C. for 20 hours. The yellow solution was cooled and poured into a mixture of ice and water (300 ml) and the mixture was acidified to pH 1 by treatment with concentrated hydrochloric acid. The brown oil which separated was extracted with diethyl ether (400 ml), the ether extract was washed with aqueous sodium carbonate solution (2N; 150 ml), dried over magnesium sulphate, and evaporated, to give a white solid (16 g), m.p 45°–50° C., consisting mainly of benzyl 2-benzyloxy-5-chlorobenzoate. This material was heated at reflux with aqueous sodium hydroxide solution (2N; 100 ml) for 3 hours. The mixture was then treated with methanol (40 ml) and heated at reflux for 6 hours. The resulting solution was neutralised to pH 7 by treatment with hydrochloric acid (2N), then concentrated under reduced pressure, acidified to pH 5 by treatment with hydrochloric acid (2N) and cooled to 10° C. The separated solid was filtered off and washed with a mixture of ice and water and recrystallized from acetic acid (100 ml) (filtering off some insoluble material) to give 2-benzyloxy-5-chlorobenzoic acid (5.23 g), m.p. 113°–115° C.

(b)(ii) The 2,5-dibenzyloxybenzoic acid used as a starting material was prepared as follows:

A mixture of methyl gentisate (16.8 g) and anhydrous potassium carbonate (7.0 g) in dry sulpholane (150 ml) was treated, with stirring, with benzyl chloride (12.7 g), and the mixture was stirred and heated at 100° C. for 4 hours. The mixture was then poured into water (800 ml) and the separated solid was filtered off and recrystallized from ethanol (with the aid of charcoal) to give methyl 5-benzyloxysalicylate (10.7 g), m.p. 108°–112° C. This ester (9.2 g) was heated at 150° C. for 3 hours with a mixture of anhydrous potassium carbonate (2.5 g) and benzyl chloride (4.52 g) in dry sulpholane (100 ml) and the mixture was then cooled and poured into a mixture of ice and water (700 ml), and the mixture was extracted with diethyl ether (2 × 300 ml). The ether extracts were combined and evaporated, the residual oil was triturated with water (100 ml), the oil was separated and the aqueous layer was extracted with diethyl ether (25 ml). The combined oil and extracts were washed with brine, dried over magnesium sulphate and evaporated to give crude methyl 2,5-dibenzyloxybenzoate (12.7 g). This ester (12.4 g) was heated at reflux with aqueous sodium hydroxide solution (2N; 400 ml) for 2 hours and allowed to cool. The separated sodium salt was filtered off and ground with hydrochloric acid (6N; 100 ml), the mixture was heated at reflux for 5 minutes and then cooled. The solid which separated was filtered off, washed with water and dried to give 2,5-dibenzyloxybenzoic acid (8.2 g), m.p. 107°–108.5° C.

(b)(iii) The 2,4-dibenzyloxybenzoic acid used as a starting material was prepared as follows:

2,4-Dihydroxybenzoic acid (48.0 g), anhydrous potassium carbonate (21.5 g), benzyl chloride (39.4 g) and dry sulpholane (400 ml) were heated together, with stirring, at 100° C. for 20 hours. The mixture was then poured into water (2 liters), the resulting oil was separated and the aqueous layer extracted with diethyl ether (300 ml). The ether extract was evaporated and its residue was combined with the said oil layer and washed with water (500 ml) to remove sulpholane, and then was washed with brine, the aqueous washings were extracted with diethyl ether (400 ml), and the combined oil and ether extract were dried and evaporated to give crude benzyl 2,4-dihydroxybenzoate (64 g), m.p. 83°–88° C. This ester (20 g) was treated with anhydrous potassium carbonate (17.0 g) and benzyl chloride (22.8 g) in dry sulpholane (300 ml) and the mixture was stirred and heated at 140° C. for 3 hours. It was allowed to cool and was then poured into water (1500 ml) and the mixture was neutralised to pH 7 by treatment with hydrochloric acid. The precipitated crude benzyl 2,4-dibenzyloxybenzoate was heated at reflux with a mixture of aqueous sodium hydroxide solution (2N; 400 ml) and ethanol (50 ml) for 10 hours. The solution was allowed to cool, and was then diluted with a large volume of water and acidified to pH 1 by treatment with hydrochloric acid (2N) to give a white solid which was filtered off and recrystallized from ethanol to give 2,4-dibenzyloxybenzoic acid (16.8 g), m.p. 126°–128° C.

(b)(iv) The 2-benzyloxy-5-methylbenzoic acid used as a starting material was prepared as follows:

5-Methylsalicylic acid was reacted with methanol and sulphuric acid by the general method of Brunner (Monatsh. 1913, 34, 916) to give methyl 5-methylsalicylate, b.p. 115°–116° C./10 mmHg. This ester (12.0 g) was heated together with benzyl chloride (9.1 g) and anhydrous potassium carbonate (5.0 g) in dry sulpholane (90 ml) at 100° C. for 22 hours. The mixture was then poured into a mixture of ice and water (1200 ml) to give crude methyl 2-benzyloxy-5-methylbenzoate (17.6 g). This ester (4.3 g) was heated at reflux with aqueous sodium hydroxide solution (2N; 100 ml) for 2 hours and the mixture was then cooled, diluted with water, and acidified to pH 2 by treatment with concentrated hydrochloric acid to give 2-benzyloxy-5-methylbenzoic acid (3.65 g), m.p. 98°–100° C.

(b)(v) The 2-benzyloxy-4-methoxybenzoic acid used as a starting material was prepared as follows:

Methyl 2,4-dihydroxybenzoate (prepared from 2,4-dihydroxybenzoic acid by the general method of Brunner (Monatsh. 1913, 34, 916) (12 g) was treated with methyl iodide (12.2 g) and anhydrous potassium carbonate (4.95 g) in dry sulpholane (140 ml) at 60°–70° C. After 8 hours, further methyl iodide (12.2 g) was added and heating was continued for 14 hours. The excess of methyl iodide was evaporated and the mixture was poured into a mixture of ice and water (1 liter) and the mixture was acidified with aqueous acetic acid (2N). The separated solid was filtered off and washed with water to give methyl 2-hydroxy-4-methoxybenzoate (10.8 g), m.p. 47°–50° C. [a sample of which, purified by chromatography on silica gel (eluting with chloroform), had the melting point 49°–51° C.]. The said crude methyl 2-hydroxy-4-methoxybenzoate (2.0 g) was heated with benzyl chloride (1.88 g) and anhydrous potassium carbonate (0.76 g) in dry sulpholane (15 ml) at 100° C. for 16 hours and was then poured into a mixture of ice and water (300 ml). The mixture was extracted with diethyl ether and the extract was washed with several portions of aqueous sodium hydroxide solution (0.5N) at 0° C., and was then dried and evaporated to give crude methyl 2-benzyloxy-4-methoxybenzoate (2.5 g) in the form of an oil. This material was heated at reflux with a mixture of aqueous sodium hydroxide solution (2N; 100 ml) and ethanol (20 ml) for 3 hours. The mixture was then treated with water (100 ml) and then cooled and extracted with diethyl ether (2 × 50 ml). The aqueous layer was cooled to 10° C. and acidified to pH 2 by treatment with concentrated hydrochloric acid to give 2-benzyloxy-4-methoxybenzoic acid (1.6 g), m.p. 99°–101° C.

REFERENCE EXAMPLE 6

2,3-Dihydroxybenzoic acid (6.16 g) and propyl iodide (6.8 g) were added to a mixture of aqueous potassium hydroxide solution (20 ml, 25% w/v), water (50 ml) and ethanol (50 ml) and the mixture was stirred and heated at reflux for 5 hours. A further quantity of propyl iodide (17 g) was then added and the mixture was again heated at reflux for 4 hours, small quantities of solid potassium hydroxide being added meanwhile in order to keep the pH at about 10. Decolourizing charcoal was then carefully added, the mixture was filtered hot and the filtrate was acidified to pH 1 by treatment with concentrated hydrochloric acid. The resulting solid was filtered off and dissolved in aqueous ammonia solution (2N), and the solution was treated with decolourizing charcoal, filtered, and the filtrate was acidified to pH 1 by treatment with hydrochloric acid to give 3-propoxysalicylic acid (5.1 g), m.p. 114°–118° C.

By proceeding in a similar manner, but replacing the propyl iodide used as a starting material by the appropriate quantity of ethyl iodide, there was prepared 3-ethoxysalicylic acid, m.p. 157° C. (recrystallized from aqueous ethanol).

REFERENCE EXAMPLE 7

By the application or adaptation of the methods described by Amin et al, J. Indian Chem, Soc., 1964, 41, 833, to 2-acetoxy-5-methylbenzoic acid, there was prepared 3-acetyl-5-methylsalicylic acid, m.p. 132°–134° C.

REFERENCE EXAMPLE 8

By proceeding in a manner similar to that hereinbefore described in Reference Example 1, there were prepared:
5-tert-butylsalicylic acid, m.p. 150°–152° C.;
5-sec-butylsalicylic acid, m.p. 65°–68° C.;
5-fluorosalicylic acid, m.p. 179°–180° C.; and
5-chlorosalicyclic acid, m.p. 171°–172° C.

REFERENCE EXAMPLE 9

By proceeding in a manner similar to that hereinbefore described in Reference Example 7, but replacing the 2-acetoxy-5-methylbenzoic acid used as starting material by the appropriate quantities of
2-acetoxy-5-chlorobenzoic acid;
2-acetoxy-5-bromobenzoic acid;
b 2-acetoxy-5-fluorobenzoic acid;
5-ethyl-2-propionyloxybenzoic acid;
2-benzoyloxy-5-methylbenzoic acid;
2-acetoxy-4,5-dimethylbenzoic acid;
2-acetoxy-5-propylbenzoic acid, and
5-methyl-2-propionyloxybenzoic acid, respectively, there were prepared:
3-acetyl-5-chlorosalicylic acid, m.p. 139°–140° C.;
3-acetyl-5-bromosalicylic acid, m.p. 145°–146° C.;
3-acetyl-5-fluorosalicylic acid, m.p. 157°–159° C.;
5-ethyl-3-propionylsalicylic acid, m.p. 135°–136° C.;
3-benzoyl-5-methylsalicylic acid, m.p. 152°–154° C.;
3-acetyl-4,5-dimethylsalicylic acid, m.p. 168°–171° C.;
3-acetyl-5-propylsalicylic acid, m.p. 95°–96° C., and
5-methyl-3-propionylsalicylic acid, m.p. 110° C.

REFERENCE EXAMPLE 10

A vigorously stirred solution of 5-tert-butyl-salicyclic acid (3.88 g) in carbon disulphide (80 ml) was treated portionwise with anhydrous aluminium chloride (8.8 g). The mixture was brought cautiously to the reflux temperature and treated with acetyl chloride (3.45 g) dropwise during 15 minutes. The mixture was heated at reflux with vigorous stirring for 20 hours and then the mixture was added to a mixture of chloroform (80 ml), ice (100 g) and concentrated hydrochloric acid (20 ml), and stirred for a further one hour. The organic layer was then separated, washed with water (3 × 20 ml), and dried over anhydrous sodium sulphate, and the solvent was removed in vacuo. The resulting solid was recrystallized from ethyl acetate, to give 3-acetyl-5-tert-butylsalicylic acid (2.3 g), m.p. 159°–161° C.

By proceeding in a similar manner, but replacing the 5-tert-butylsalicylic acid, used as a starting material, by the appropriate quantity of 5-sec-butylsalicylic acid, there was prepared 3-acetyl-5-sec-butylsalicylic acid m.p. 131°–133° C. (recrystallized from ethyl acetate at a low temperature).

REFERENCE EXAMPLE 11

The preparation of 5-formylsalicylic acid was carried out by the application of the method described for its preparation by Wayne et al, J. Chem. Soc., 121, 1022, (1922). 3-Formylsalicylic acid was obtained from the mother liquors by means of the insoluble barium salt.

REFERENCE EXAMPLE 12

3-Formyl-5-methylsalicylic acid, m.p. 190°–194° C. (recrystallized from aqueous methanol) was prepared from 5-methylsalicylic acid by the application of methods described in the specification of U.S. Pat. No. 3,833,660.

REFERENCE EXAMPLE 13

3-Formyl-2-hydroxyacetophenone (15.0 g) was added to a stirred suspension of freshly prepared argentous oxide (23.15 g) in aqueous sodium hydroxide solution (0.9N; 300 ml) at between 5° and 10° C. during a period of one hour. The mixture was then stirred for a further period of one hour. After filtration to remove the silver, the resulting orange solution was treated with charcoal and filtered, and was then acidified by treatment with concentrated hydrochloric acid. The resulting precipitate was collected and recrystallized from water, with the aid of charcoal, to give 3-acetylsalicylic acid (9.4 g), m.p. 135°–136° C.

The 3-formyl-2-hydroxyacetophenone, used as starting material, was prepared as follows:

A solution of 2-hydroxy-3-propenylacetophenone (40.9 g) in dry ethyl acetate (600 ml) was cooled to between −65° and −70° C. A stream of oxygen, containing about 2% of of ozone, was then passed through until the yellow colour of the solution has disappeared, and a white precipitate had formed, and until no more ozone was being absorbed (as was indicated by the sudden liberation of iodine from a potassium iodide test solution by the outflowing gas). Dimethyl sulphide (60 ml) was then added and the mixture was allowed to warm up to room temperature during 2 hours and was then left to stand at room temperature for 15 hours. The solvents were removed in vacuo and water (200 ml) was added to the residue. The resulting solid was extracted with diethyl ether (250 ml). The ether layer was washed with water (3 × 20 ml), and dried over anhydrous sodium sulphate, and then the solvent was removed in vacuo. The residue was recrystallized from a mixture of petroleum ether (b.p. 60°–80° C.) and carbon tetrachloride to give 3-formyl-2-hydroxyacetophenone (20.0 g), m.p. 67°–69° C.

The 2-hydroxy-3-propenylacetophenone, used as starting material, was prepared as follows:

A solution of 3-allyl-2-hydroxyacetophenone (100 g) in toluene (300 ml) was treated with bis(benzonitrile) palladous chloride (5 g). The mixture was heated at reflux for 20 hours. The mixture was then filtered and the solvent was removed from the filtrate in vacuo. Fractional distillation of the resulting oil gave 2-hydroxy-3-propenylacetophenone (90 g), b.p. 153°–155° C./18 mmHg.

The 3-allyl-2-hydroxyacetophenone used as starting material was prepared according to methods described by Takuhashi et al, J. Pharm. Soc. Japan, 74, 48–51 (1954).

REFERENCE EXAMPLE 14

N,N'-Dicyclohexylcarbodiimide (1.03 g) was added to a solution of 2-benzyloxy-5-trifluoromethylbenzoic acid (1.48 g) and anhydrous 5-aminotetrazole (0.425 g) in dry pyridine (25 ml), and the resulting mixture was stirred at room temperature for 20 hours. The pyridine was removed in vacuo and the residue was treated with ammonia solution (4N; 75 ml) and stirred for one hour. The insoluble N,N'-dicyclohexylurea was filtered off, and the filtrate was acidified by treatment with concentrated hydrochloric acid. The precipitated solid was recrystallized from ethanol to give 2-benzyloxy-5-trifluoromethyl-N-(tetrazol-5-yl)benzamide (1.25 g), m.p. 248°–249° C. (with decomposition).

The 2-benzyloxy-5-trifluoromethylbenzoic acid, used as starting material, was prepared as follows:

Sodium hydride powder (0.08 g) was added to dry benzyl alcohol (15 ml) and the mixture was warmed in order to complete the resulting reaction. The mixture was then treated with 2-chloro-5-trifluoromethylbenzonitrile (0.62 g) and was heated, with stirring, at between 90° and 95° C. for 20 hours. The mixture was then diluted with benzyl alcohol (10 ml), the mixture was filtered, and the filtrate was evaporated under vacuum. The resulting oil was then treated with a solution of sodium hydroxide (6 g) in aqueous ethanol (95%; 30 ml) and heated at reflux. The solvent was removed in vacuo, water (25 ml) and diethyl ether (25 ml) were added to the residue, the mixture was agitated and the layers were separated.

The aqueous layer was then acidified by treatment with concentrated hydrochloric acid. The precipitate was filtered off and recrystallized from water to give 2-benzyloxy-5-trifluoromethylbenzoic acid (0.35 g), m.p. 94°–95° C.

The 2-chloro-5-trifluoromethylbenzonitrile, used as starting material, was prepared by adaptation of the methods of Garder et al, Arzneimittel Forschung, 13, 802 (1963).

REFERENCE EXAMPLE 15

Trifluoroacetic acid (0.8 ml) was added to dry 2,6-lutidine (10 ml) and the mixture was then treated with 3-cyano-5-methylsalicylic acid (0.885 g), sodium azide (0.65 g) and lithium chloride (20 mg), and heated at reflux for 20 hours. The mixture was then diluted with water (20 ml) and acidified by treatment with concentrated hydrochloric acid. The resulting precipitate was collected and recrystallized from a large amount of acetic acid to give 5-methyl-3-(tetrazol-5-yl)salicylic acid (0.65 g), m.p. 290°–292° C. (with decomposition).

REFERENCE EXAMPLE 16

3-Formyl-5-methylsalicylic acid (3.6 g) was dissolved in dimethylformamide (20 ml) and treated with hydroxylamine hydrochloride (1.53 g). The mixture was heated at reflux for 10 minutes and then the solvent was removed in vacuo. The residue was treated with water (20 ml) and hydrochloric acid (2N; 10 ml). The precipitated solid was filtered off and recrystallized from aqueous ethanol to give 3-cyano-5-methylsalicylic acid (2.7 g), m.p. 193°–194° C.

By proceeding in a similar manner, but replacing the 3-formyl-5-methylsalicylic acid, used as a starting material, by the appropriate quantities of 3-formylsalicylic acid and 5-formylsalicylic acid, respectively, there were prepared 3-cyanosalicylic acid, m.p. 213°–214° C., and 5-cyanosalicylic acid, m.p. 217°–220° C.

REFERENCE EXAMPLE 17

A suspension of 3-aminosalicylic acid (5.0 g) in acetic acid (75 ml) was treated with hydrochloric acid (2N), slowly with shaking, until complete solution was achieved. The solution was then treated with aqueous formaldehyde solution (40% w/v; 20 ml) and 5% palladium on charcoal catalyst (2.0 g), and the mixture was hydrogenated at 25° C. and at atmospheric pressure for 18 hours. The catalyst was filtered off, the filtrate was evaporated in vacuo, and the resulting residue was dissolved in hydrochloric acid (2N; 100 ml) and then the solution was adjusted to pH 5 by treatment with concentrated aqueous ammonia solution. The mixture was left to stand for 24 hours in the refrigerator. The precipitate was then collected to give 3-dimethylaminosalicylic acid (3.0 g), m.p. 273°–277° C. (with decomposition).

REFERENCE EXAMPLE 18

Benzyl chloroformate (5.5 g) was added to a suspension of 5-aminosalicylic acid (4.6 g) in dry pyridine (25 ml) at 0° C. during a period of 5 minutes. The mixture was allowed to warm to 25° C. and was stirred for 20 hours, and was then poured into a mixture of ice (100 g) and concentrated hydrochloric acid (50 ml). The solid that precipitated was then filtered off and dissolved in ethanol (50 ml) and treated with a little charcoal. The mixture was filtered and the filtrate was evaporated to dryness to give 5-benzyloxycarbonylaminosalicylic acid (2.2 g), m.p. 222°–224° C.

By proceeding in a similar manner, but replacing the 5-aminosalicylic acid, used as a starting material, by the appropriate quantity of 4-aminosalicylic acid, there was prepared 4-benzyloxycarbonylaminosalicylic acid, m.p. 184°–186° C.

REFERENCE EXAMPLE 19

2-Hydroxyisophthalic acid (1.82 g) and N,N'-dicyclohexylcarbodiimide (2.17 g) were dissolved together in dry pyridine (30 ml) and the mixture was stirred for 2 hours at room temperature. The mixture was then treated with dry tert-butylamine (5 ml), and the mixture was stirred at 60° C. for 20 hours. The solvents were removed in vacuo, and the residue was treated with saturated aqueous sodium bicarbonate solution (50 ml). The mixture was stirred for 15 minutes. The insoluble N,N'-dicyclohexylurea was then removed by filtration and the resulting filtrate was treated with charcoal and filtered again. The filtrate was then acidified by treatment with concentrated hydrochloric acid to give a white solid which was filtered off and recrystallized from a mixture of petroleum ether (b.p. 60°–80° C.) and benzene to give 3-tert-butylcarbamoylsalicylic acid (1.2 g), m.p. 191°–195° C.

REFERENCE EXAMPLE 20

5-Acetylsalicylic acid (9.0 g) was dissolved in concentrated sulphuric acid (20 ml). The solution was cooled to 0° C. and treated, with stirring, with a mixture of concentrated nitric acid (density 1.42; 3.8 ml) and concentrated sulphuric acid (3.8 ml), dropwise, at such a rate that the temperature did not exceed 5° C. The mixture was left to stand at 0° C. for 5 hours and then it was poured onto a mixture of ice and water (100 ml). The precipitated solid was filtered off and recrystallized from water to give 5-acetyl-3-nitrosalicylic acid (8.6 g), m.p. 192°–193° C.

REFERENCE EXAMPLE 21

3,5-Diacetyl-2,4-dihydroxybenzoic acid was prepared according to the methods described by Amin et al., J. Ind. Chem. Soc., 29, 351 (1952).

The present invention includes within its scope pharmaceutical compositions which comprise one or more compounds of formula I together with a pharmaceutical carrier or coating. In clinical practice the compounds of the present invention will normally be administered orally, sub-lingually, nasally, rectally or parenterally.

Solid compositions for oral administration include compressed tablets, pills, dispersible powders, and granules. In such solid compositions the active compound or compounds is or are mixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically acceptable emulsions, solutions, suspensions, and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing the active compound or compounds with or without the addition of diluents or excipients.

The compound(s) may also be administered sublingually by administration of relatively slowly dissolving tablets which, besides including inert diluents as commonly used in the art, may contain sweetening, flavouring, perfuming and preserving agents.

Solid compositions for rectal administration include suppositories formulated in manner known per se and containing the active compound or compounds.

Preparations according to the invention for parenteral administration include sterile aqueous or nonaqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilised, for example, by filtration through a bacteria-retaining filter, by incorporation of sterilising agents in the compositions, by irradiation, or by heating. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. Generally the compositions should contain 0.1% to 50% by weight of benzene derivative, especially when in tablet form. When in aerosol form as hereinafter described the compositions should contain 0.2 to 5%, preferably 2 to 5%, by weight of benzene derivative.

The active compound or compounds may also be administered by methods known for the inhalation of drugs which are not themselves gaseous under normal conditions of administration. Thus, a solution of the compound or compounds in a suitable pharmaceutically acceptable solvent, for example water, can be nebulized by a mechanical nebulizer, for example a Wright Nebulizer, to give an aerosol of finely-divided liquid particles suitable for administration for inhalation orally or nasally. The solutions may contain stabilizing agents and buffering agents to give an isotonic character, e.g. sodium chloride, sodium citrate and citric acid.

Means for producing self-propelling compositions for generating aerosols for the administration of medicaments are, for example, described in detail in U.S. Pat. Nos. 2,868,691 and 3,095,355.

The compound or compounds may also be administered orally by inhalation in the form of a dry micronised powder, which may be diluted with one or more suitable pharmaceutically acceptable inert solid diluents selected from, for example, lycopodium, boric acid, starch, bismuth subcarbonate and heavy magnesium carbonate.

The pharmaceutical compositions of the present invention may contain, in addition to the compound or compounds of formula I, one or more substances known per se to have bronchodilating actions in man, for example, isoprenaline, salbutamol and prostaglandin $E_1$ ($PGE_1$).

It is highly desirable that the aerosols or micronised powders should have a particle size less than about 10 microns and preferably less than 5 microns, for example, between 0.5 and 3 microns, to ensure effective distribution to very narrow bronchioles. Preferably, administration is by means of devices enabling controlled quantities of the active ingredients to be administered, for example by means of metered valves.

The dose of the compounds of general formula I employed depends upon the desired therapeutic effect, the route of administration and the duration of the treatment. In the adult, the doses are generally between 0.02 and 4 mg/kg body weight per day by administration by inhalation in divided doses, and generally between 4 and 2000, preferably between 4 and 400 mg/kg body weight per day by oral administration.

The following Composition Examples illustrate pharmaceutical compositions according to the present invention.

COMPOSITION EXAMPLE 1

Micromilled 2-hydroxy-3-methoxy-N-(tetrazol-5-yl)benzamide (600 mg) and emulsifier YN (150 mg; a mixture of ammonium compounds of phosphatidic acids derived from rape seed oil) were placed in an aluminium vial (20 ml capacity). Trichloromonofluoromethane (2.7 g), dichlorodifluoromethane (9.4 g) and dichlorotetrafluoroethane (4.4 g) were then added, to give a total volume of 12.5 ml. The vial was sealed with a metered valve delivering a dose of 0.05 ml. Each dose (generated from 0.05 ml of suspension) of aerosol released from the pressurized pack thus obtained contained 2.4 mg of 2-hydroxy-3-methoxy-N-(tetrazol-5-yl)benzamide.

COMPOSITION EXAMPLE 2

Capsules for oral administration were made up in the usual manner by filling No. 2 size gelatine capsules each with 255 mg of the following composition:

| | |
|---|---|
| 3-acetyl-2-hydroxy-5-methyl-N-(tetrazol-5-yl)benzamide | 150 mg |
| lactose | 50 mg |
| starch | 50 mg |
| magnesium stearate | 2.5 mg |
| aerosil | 2.5 mg |

We claim:

1. A compound of the formula:

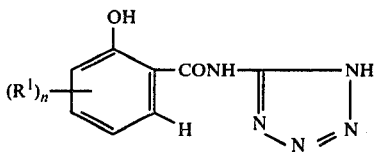

wherein $R^1$ represents a fluorine, chlorine or bromine atom, or an alkyl, alkoxy, alkylthio, alkylsulphonyl, alkanoylamino, alkylamino or alkylsulphamoyl group, each such group containing from 1 to 6 carbon atoms, a dialkylsulphamoyl, dialkylamino or dialkylcarbamoyl group wherein the two alkyl groups may be the same or different and each contains from 1 to 4 carbon atoms, an alkanoyl, alkoxycarbonyl, alkoxycarbonylamino or alkylcarbamoyl group containing from 2 to 6 carbon atoms, or a hydroxy, formyl, nitro, trifluoromethyl, phenyl, benzyloxycarbonylamino, amino, sulphamoyl, cyano, tetrazol-5-yl, carboxy, carbamoyl or benzoyl group, and n represents 1 or 2, the substituents $R^1$ being in the 3- and 5-positions when n represents 2, and pharmaceutically acceptable salts thereof.

2. A compound according to claim 1 wherein $R^1$ represents a fluorine, chlorine or bromine atom, an alkyl, alkoxy, alkylthio, alkylsulphonyl or alkanoylamino group, each such group containing from 1 to 6 carbon atoms, a dialkylsulphamoyl group wherein the two alkyl groups may be the same or different and each contains from 1 to 4 carbon atoms, an alkanoyl group containing from 2 to 6 carbon atoms, or a hydroxy, formyl, nitro, trifluoromethyl or phenyl group, and n represents 1 or 2, the substituents $R^1$ being in the 3- and 5-positions when n represents 2, and pharmaceutically acceptable salts thereof.

3. A compound according to claim 1 wherein $R^1$ represents a fluorine, chlorine or bromine atom, or an alkyl, alkoxy, alkylthio, alkylsulphonyl, alkanoylamino or alkylsulphamoyl group, each such group containing from 1 to 6 carbon atoms, a dialkylsulphamoyl or dialkylamino group wherein the two alkyl groups may be the same or different and each contains from 1 to 4 carbon atoms, an alkanoyl or alkylcarbamoyl group containing from 2 to 6 carbon atoms, or a hydroxy, formyl, nitro, trifluoromethyl, phenyl, benzyloxycarbonylamino, amino, sulphamoyl, cyano, tetrazol-5-yl, carboxy or benzoyl group, and n represents 1 or 2, the substituents $R^1$ being in the 3- and 5-positions when n represents 2 and pharmaceutically acceptable salts thereof.

4. A compound according to claim 1 wherein one of the substituents $R^1$ on the phenyl ring of the compounds of the general formula depicted in claim 1 is a nitro, cyano, alkanoyl, formyl or tetrazol-5-yl group, any other substituent $R^1$ present on the phenyl ring being as defined in claim 1, and pharmaceutically acceptable salts thereof.

5. A compound according to claim 1 which is 3-acetyl-2-hydroxy-5-methyl-N-(tetrazol-5-yl)benzamide and pharmaceutically acceptable salts thereof.

6. A compound according to claim 1 which is 2-hydroxy-3-methoxy-N-(tetrazol-5-yl)benzamide and pharmaceutically acceptable salts thereof.

7. A compound according to claim 1 which is 3-acetyl-5-ethyl-2-hydroxy-N-(tetrazol-5-yl)benzamide and pharmaceutically acceptable salts thereof.

8. A compound according to claim 1 which is 3-acetyl-2-hydroxy-N-(tetrazol-5-yl)benzamide and pharmaceutically acceptable salts thereof.

9. A compound according to claim 1 which is 3-acetyl-2-hydroxy-5-propyl-N-(tetrazol-5-yl)benzamide and pharmaceutically acceptable salts thereof.

10. A compound according to claim 1 which is 2-hydroxy-5-methyl-3-propionyl-N-(tetrazol-5-yl)benzamide and pharmaceutically acceptable salts thereof.

11. A compound according to claim 1 which is 5-ethyl-2-hydroxy-3-propionyl-N-(tetrazol-5-yl)benzamide and pharmaceutically acceptable salts thereof.

12. A compound according to claim 1 which is 2-hydroxy-5-methyl-3,N-bis(tetrazol-5-yl)benzamide and pharmaceutically acceptable salts thereof.

13. A compound according to claim 1 which is 3-acetyl-2-hydroxy-5-nitro-N-(tetrazol-5-yl)benzamide and pharmaceutically acceptable salts thereof.

14. A compound according to claim 1 which is 2-hydroxy-3,5-dinitro-N-(tetrazol-5-yl)benzamide and pharmaceutically acceptable salts thereof.

15. A compound according to claim 1 which is 2-hydroxy-3-nitro-N-(tetrazol-5-yl)benzamide and pharmaceutically acceptable salts thereof.

16. A compound according to claim 1 which is 2-hydroxy-3-propoxy-N-(tetrazol-5-yl)benzamide and pharmaceutically acceptable salts thereof.

17. A compound according to claim 1 which is 2-hydroxy-5-nitro-N-(tetrazol-5-yl)benzamide and pharmaceutically acceptable salts thereof.

18. A compound according to claim 1 which is 2-hydroxy-5-methoxy-N-(tetrazol-5-yl)benzamide and pharmaceutically acceptable salts thereof.

19. A compound according to claim 1 which is 4-acetylamino-2-hydroxy-N-(tetrazol-5-yl)benzamide and pharmaceutically acceptable salts thereof.

20. A compound according to claim 1 which is 2-hydroxy-5-methylthio-N-(tetrazol-5-yl)benzamide and pharmaceutically acceptable salts thereof.

21. A compound according to claim 1 which is 5-formyl-2-hydroxy-N-(tetrazol-5-yl)benzamide and pharmaceutically acceptable salts thereof.

22. A compound according to claim 1 which is 4-benzyloxycarbonylamino-2-hydroxy-N-(tetrazol-5-yl)benzamide and pharmaceutically acceptable salts thereof.

23. A compound according to claim 1 which is 3-acetyl-2-hydroxy-5-sulphamoyl-N-(tetrazol-5-yl)benzamide and pharmaceutically acceptable salts thereof.

24. A compound according to claim 1 which is 3-acetyl-5-sec-butyl-2-hydroxy-N-(tetrazol-5-yl)benzamide and pharmaceutically acceptable salts thereof.

25. A compound according to claim 1 which is 3-acetyl-5-tert-butyl-2-hydroxy-N-(tetrazol-5-yl)benzamide and pharmaceutically acceptable salts thereof.

26. A compound according to claim 1 which is 3-acetyl-5-fluoro-2-hydroxy-N-(tetrazol-5-yl)benzamide and pharmaceutically acceptable salts thereof.

27. A compound according to claim 1 which is 3-butyryl-5-ethyl-2-hydroxy-N-(tetrazol-5-yl)benzamide and pharmaceutically acceptable salts thereof.

28. A compound according to claim 1 which is 3-formyl-2-hydroxy-N-(tetrazol-5-yl)benzamide and pharmaceutically acceptable salts thereof.

29. A compound according to claim 1 which is 3-cyano-2-hydroxy-N-(tetrazol-5-yl)benzamide and pharmaceutically acceptable salts thereof.

30. A compound according to claim 1 which is 5-cyano-2-hydroxy-N-(tetrazol-5-yl)benzamide and pharmaceutically acceptable salts thereof.

31. A compound according to claim 1 which is 5-acetyl-2-hydroxy-3-nitro-N-(tetrazol-5-yl)benzamide and pharmaceutically acceptable salts thereof.

32. A pharmaceutical composition useful in the treatment of respiratory disorders manifested by the interaction of tissue-fixed antibodies with specific antigens which comprises as active ingredient, an effective amount of a compound as claimed in claim 1, or a pharmaceutically acceptable salt thereof, in association with a pharmaceutical carrier.

* * * * *